(12) United States Patent
Tsukada

(10) Patent No.: US 7,569,366 B2
(45) Date of Patent: Aug. 4, 2009

(54) PCR AMPLIFICATION REACTION APPARATUS AND METHOD FOR PCR AMPLIFICATION REACTION USING APPARATUS

(75) Inventor: Mamoru Tsukada, Kanagawa-ken (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/111,904

(22) Filed: Apr. 22, 2005

(65) Prior Publication Data

US 2005/0239119 A1    Oct. 27, 2005

(30) Foreign Application Priority Data

Apr. 26, 2004    (JP)    ............... 2004-130041

(51) Int. Cl.
*C12P 19/34* (2006.01)
*C12M 1/00* (2006.01)

(52) U.S. Cl. .................. 435/91.2; 435/6; 435/283.1

(58) Field of Classification Search .................. None
See application file for complete search history.

(56) References Cited

U.S. PATENT DOCUMENTS

| 4,415,732 | A | 11/1983 | Caruthers et al. |
| 5,656,493 | A * | 8/1997 | Mullis et al. ............ 435/286.1 |
| 2002/0009716 | A1 | 1/2002 | Abarzua |
| 2002/0197603 | A1* | 12/2002 | Chow et al. ............ 435/6 |
| 2003/0013868 | A1 | 1/2003 | Huang et al. |
| 2003/0017482 | A1* | 1/2003 | Godfrey et al. ............ 435/6 |
| 2003/0094953 | A1* | 5/2003 | Brooks et al. ............ 324/441 |
| 2003/0194228 | A1* | 10/2003 | Bradenbaugh ............ 392/463 |
| 2004/0038206 | A1 | 2/2004 | Zhang et al. |
| 2004/0132080 | A1 | 7/2004 | Kawaguchi et al. |
| 2004/0161741 | A1* | 8/2004 | Rabani et al. ............ 435/6 |
| 2004/0241643 | A1 | 12/2004 | Yamamoto et al. |
| 2005/0064423 | A1 | 3/2005 | Higuchi et al. |
| 2005/0143930 | A1 | 6/2005 | Tsukada |

FOREIGN PATENT DOCUMENTS

| EP | 1 275 438 | 1/2003 |
| EP | 1 304 388 | 4/2003 |
| WO | 94/05414 | 3/1994 |
| WO | 01/08800 | 2/2001 |
| WO | 03/057875 | 7/2003 |
| WO | 04/001412 | 12/2003 |
| WO | WO 03102226 A1 * | 12/2003 |

* cited by examiner

*Primary Examiner*—Young J Kim
*Assistant Examiner*—Samuel Woolwine
(74) *Attorney, Agent, or Firm*—Fitzpatrick, Cella, Harper & Scinto

(57) ABSTRACT

The present invention provides a method for PCR amplification reaction that can reduce the time required for amplification reaction of nucleic acid by PCR using the target nucleotide molecule as a template, and an apparatus used for the method. The method comprises using a PCR reaction vessel in which a heater for local heating, which can thermally contact with a solution storing section with an extremely small capacity for storing a PCR reaction solution and a reaction solution stored in the solution storing section directly, is placed; feeding a pulsed current to the placed heater; and carrying out a thermal cycle of PCR reaction, so that high-speed PCR amplification reaction can be carried out.

6 Claims, 4 Drawing Sheets

PCR AMPLIFICATION REACTION APPARATUS AND METHOD FOR PCR AMPLIFICATION REACTION USING APPARATUS

BACKGROUND OF THE INVENTION

1. Field of the Invention

The present invention relates to a PCR amplification reaction apparatus and a method for PCR amplification reaction using the apparatus. Particularly, the present invention relates to a PCR amplification reaction apparatus that can be used for analyzing a genetic polymorphism, a single nucleotide genetic polymorphism (SNP) or the like, to a method for PCR amplification reaction using the apparatus, and to a method for detecting a genetic polymorphism, an SNP or the like to which the apparatus and/or the method are applied.

2. Related Background Art

Conventionally, PCR (polymerase chain reaction) has been used as typical means for amplifying a specific region of a nucleic acid chain. PCR comprises adding a DNA polymerase enzyme and each nucleic acid as a substrate to a region to be amplified of a template nucleic acid chain, for example, a double-strand DNA using a corresponding DNA fragment called a PCR primer corresponding to the partial nucleotide sequences of both terminals of the region, and repeating a thermal cycle consisting of denaturing, annealing and extension to amplify only the DNA strand of a target region. A one-cycle process consisting of, for example, denaturing at 94° C. for 30 seconds, annealing at 55° C. for 30 seconds and extension at 72° C. for one minute as the thermal cycle for PCR reaction is repeated 30 times in total. Under these conditions, the time required for the thermal cycles as a whole is about 1.5 hours. When amplifying a nucleic acid chain in which a region to be amplified has a larger length of nucleotides, the time interval for the extension step carrying out reaction of extending a DNA strand from the 3'-end of a primer is set longer. Accordingly, it is fairly general that the total time required for the thermal cycles amounts to about 1.5 to 2.5 hours.

In order to reduce as much as possible the time for such a thermal cycle process requiring a long period of time, several contrivances have been proposed. For example, Light Cycler (Roche Diagnostics), an apparatus in which amplification reaction is completed within about 20 to 30 minutes has been commercially available in recent years. However, the time reduction technique used in this commercially available apparatus is a technique of applying temperature controlled hot air to a capillary vessel simply in order to reduce the time spent for temperature change. Specifically, the technique reduces the time spent for temperature change based on the finding that use of a capillary vessel can reduce the volume of the reaction vessel and a capillary vessel has a small heat capacity. The temperature controlling technique itself is, in principle, the same as a conventional technique. In addition, air used as a heating and cooling medium in this apparatus has a small density and a small thermal conductivity and is one of the least heat conductive media. Taking these points into consideration, it cannot be said that air is not an optimal temperature controlling system.

On the other hand, the greatest advantage of PCR is that the method can selectively amplify a nucleic acid chain having a specific nucleotide sequence in a sample containing various nucleic acid chains collected from the living body. In analysis of genetic polymorphisms, SNPs or the like, only the nucleic acid chain which indicates a difference of nucleotide sequences to be analyzed must be selectively amplified in a sample containing various nucleic acid chains prior to the analysis. In a process for preparing this DNA sample for analysis, PCR amplification has been widely used with the above-described selectivity against a nucleotide sequence.

Conventionally, there has been no technique for analyzing gene polymorphisms, SNPs or the like that is specifically limited based on nucleotide sequences. For analysis of various genetic polymorphisms, SNPs or the like, used is an oligonucleotide fragment for a detection probe which corresponds to a partial nucleotide sequence that is known to exhibit a difference based on technological accumulation in the past. In a technology similar to a microarray technology, about 100 kinds of bead arrays of Luminex Corp. or electrode arrays of Nanogen, Inc. are used in order to achieve a hybridization reaction time remarkably shorter as compared with a conventional microarray technology.

Other than the microarray technology using hybridization reaction with a detection probe, several analysis technologies have been known. An RFLP (Restriction Fragment Length polymorphism) technology comprises effecting a restriction enzyme that can cleave a partial nucleotide sequence indicating a difference on a selectively amplified double-strand DNA, and judging whether or not the corresponding partial nucleotide sequence exists based on the difference in electrophoresis patterns among a plurality of DNA fragments produced. Direct nucleotide sequence determination comprises PCR amplifying using a Dye terminator for a DNA sequencer with a nucleic acid chain containing genetic polymorphisms, SNPs or the like as a template and directly determining the nucleotide sequence with a DNA sequencer to judge whether or not the partial nucleotide sequence indicating a difference exists.

In the RFLP technology, a restriction enzyme that can cleave a partial nucleotide sequence indicating a difference between detectable genetic polymorphisms is required to be selected and used. Accordingly, the technology has a methodologically limited range of application, for example, can be applied only to a case where a difference is indicated by a partial nucleotide sequence corresponding to the site of an available restriction enzyme. On the other hand, there are no limitations, in principle, to the application range for the direct nucleotide sequence determination, because a DNA sequencer is actually used to determine the nucleotide sequence. However, when a template contains a plurality of similar sequences, it is difficult to analyze a single gene, and a problem of ambiguity found in some HLA typings occurs. In addition, the time required for pretreatment of a sample used for DNA sequencing, the running cost for a DNA sequencer apparatus, and the electrophoresis time of the technology are disadvantageous for working efficiency and economical efficiency. In particular, the number of genetic polymorphisms that can be analyzed at the same time is limited according to the number of capillaries in a DNA sequencer apparatus. On the other hand, when the number of capillaries is smaller than that of samples to be analyzed, the apparatus suffers from reduced operation efficiency. Taking these limitations into consideration, it is hard to say that direct nucleotide sequence determination is not an optimal technology.

On the other hand, the technology with a microarray can analyze a plurality of probes ranging from several thousand dots to ten thousand dots in one time, advantageously. In contrast, a nucleic acid chain to be detected by each probe must be labeled such as fluorescently labeled. Such a pretreatment of a sample requires several hours as in the case of direct nucleotide sequence determination, and such a pretreatment must be carried out for each objective probe, which leads to a complicated work. Moreover, the probe hybridization reaction on a microarray is carried out as a solid phase reaction and requires several hours. Furthermore, if the length of the DNA strand of a sample is too much larger than the length of probes involved in hybridization, crossreaction with other probes may be induced. It is true that the technology with a bead array or electrode array is means for significantly improving the probe hybridization reaction time. However, it is difficult to prepare a large-scale probe array like a conventional microarray, and only about 100 kinds of probe arrays are available. For examples, regarding to HLA genetic polymorphisms, two hundred and several ten kinds of alleles have been already confirmed. The technology with a bead array or electrode array cannot be adequately applied to analysis of such many kinds.

SUMMARY OF THE INVENTION

As described above, conventional techniques for analyzing genetic polymorphisms, SNPs or the like can be adequately applied to individual application fields, but any of the techniques has advantages and drawbacks when the technique is to be widely applied.

For use of any of the analysis techniques, it has been desired to reduce the time required for pretreatment of a sample, specifically, the time spent for PCR amplification reaction for selectively amplifying only the nucleic acid chain indicating a difference between the nucleotide sequences to be analyzed.

In addition, the technology with a microarray can analyze many kinds of probes in one time, advantageously, but has been desired to allow further reduction in both the time required for pretreatment of a sample and the time required for probe hybridization reaction on a microarray, when the technology is to be widely applied.

The present invention has achieved to solve these problems. A first object of the present invention is to provide a novel PCR amplification apparatus that is used for pretreatment a sample and can significantly reduce the time spent for PCR amplification reaction, and a method for PCR amplification using the apparatus. In addition, a second object of the present invention is to provide a novel method for detecting DNA in SNPs and genetic polymorphisms to which such a novel PCR amplification apparatus and such a method for PCR amplification using the apparatus can be applied and which can detect genetic polymorphisms or SNPs sensitively, simultaneously, and more conveniently in a shorter processing time with a probe fixed on a microarray.

Prior to conducting investigations on means for achieving the first object, the present inventors have reviewed which step of a thermal cycle in PCR amplification reaction is a rate-determining step. In general, PCR amplification reaction employs a thermal cycle consisting of hybridization reaction of a template single-strand nucleic acid molecule with a primer, specifically, an annealing step of forming a double strand in which the single-strand nucleic acid molecule binds to the complementary strand; an extension step of effecting a DNA polymerase enzyme after the hybridization to carry out reaction of extending a DNA strand from the 3'-end of the primer constituting such a double strand; and a denaturing step of thermally dissociating the double-strand nucleic acid after the extension reaction to separate the nucleic acid into a template single-strand nucleic acid molecule and its complementary strand. The inventors have found that in this case, in the extension step of effecting a DNA polymerase enzyme after the hybridization to carry out reaction of extending a DNA strand from the 3'-end of the primer constituting such a double strand, the time for completing the extension reaction of a DNA strand by the DNA polymerase enzyme to accomplish the synthesis of the complementary strand determines the rate of the entire amplification reaction. On the other hand, the inventors have found that, by setting sufficiently high the temperature for the denaturing step of thermally dissociating the double-strand nucleic acid to separate the nucleic acid into a template single-strand nucleic acid molecule and its complementary strand, thermal dissociation of the most part of the double strand can be completed even if the heating time is several ten ms.

In the hybridization reaction of a single-strand nucleic acid molecule with a primer, misfit hybridization, in which the primer hybridizes with a part other than the nucleotide sequence part complementary to the primer, may accidentally occur, usually. Misfit hybridization is avoided by selecting a temperature that does not cause misfit hybridization of a primer as the temperature for the annealing step by using the difference between the Tm value (melting temperature) of a primer that hybridizes with a full-match sequence and the Tm value of a primer that misfit hybridizes with a mismatch sequence. In this case, the temperature of the extension step is appropriately selected so that the temperature is the Tm value (melting temperature) of a primer that hybridizes with a full-match sequence or lower or the temperature for the annealing step or higher, according to the rate of DNA strand extension reaction by a DNA polymerase enzyme.

The inventors have found taking the above facts into consideration that the time required for one thermal cycle can be remarkably reduced, if the thermal cycle process can comprise preheating a reaction solution as a whole to a temperature for the annealing step, heating the reaction solution to a temperature above the target denaturing temperature for several ten ms in the denaturing step, and then rapidly cooling the reaction temperature to the temperature for the annealing step. Based on this finding, the inventors have accomplished the invention of the method for PCR amplification reaction according to a first embodiment of the present invention.

Specifically, the method for PCR amplification reaction according to the first embodiment of the present invention is a method for PCR amplification reaction comprising amplifying, from a nucleic acid chain as a template, a DNA strand having a corresponding nucleotide sequence by PCR reaction, the PCR amplification reaction comprising:

using, as a reaction vessel for storing a PCR reaction solution containing the nucleic acid chain as a template, a reaction vessel in which a heater is placed at a position at which the heater can thermally contact the stored reaction solution;

storing the PCR reaction solution of the designed storing capacity in a solution storing section of the reaction vessel with a heater;

bringing the entire reaction vessel with the heater into contact with a medium set at a predetermined temperature to maintain the vessel at the predetermined temperature in a continuous manner;

applying a predetermined pulsed voltage to the heater provided in the reaction vessel and carrying out pulsed heating corresponding to the pulse time width and the pulse voltage height to form a thermal cycle for PCR reaction; and providing a process of carrying out PCR reaction by repeating application of the pulsed voltage a plurality of times and correspondingly repeating the thermal cycle a plurality of times.

The reaction vessel preferably has a storing capacity of the reaction solution and a shape of the solution storing section designed in order to exhibit a heat capacity in which the temperature of the reaction solution can respond to the thermal pulse generated by applying a predetermined pulsed voltage to the heater in the order of at least 0.01 second. The process of carrying out PCR reaction preferably repeats application of the pulsed voltage a plurality of times periodically and correspondingly repeats the thermal cycle a plurality of times.

The present invention provides a PCR apparatus for realizing the above method.

Specifically, the apparatus for carrying out PCR amplification reaction according to the present invention comprises:

a reaction vessel for storing a PCR reaction solution;

a heater placed at a position at which the heater can thermally contact the stored reaction solution;

a pulsed voltage generating mechanism for applying a predetermined pulsed voltage to the heater; and a block that has a structure in which the reaction vessel with the heater can be held, and can maintain the entire reaction vessel at a predetermined temperature in a continuous manner through thermal conduction by bringing the reaction vessel into contact with the reaction vessel.

The heater is preferably placed at a position at which the heater can thermally contact the stored reaction solution directly.

The heater is suitably constituted as laminated on at least a part of the inner wall of the reaction vessel.

The apparatus preferably comprises a heating block temperature control mechanism for controlling the temperature of the heating block at a predetermined temperature.

Furthermore, the apparatus suitably comprises an MPU unit for managing the operation of the heating block temperature control mechanism and the pulsed voltage generating mechanism;

a key input device for inputting and setting the managing conditions by the MPU unit; and a display for displaying the managing conditions by the MPU unit or the managed status information.

Next, prior to conducting investigations on means for achieving the second object, the present inventors have studied means for inhibiting progress of reaction of extending a DNA strand from the 3'-end of a primer misfit that hybridizes with a template nucleic acid molecule by a DNA polymerase enzyme in PCR amplification reaction. It is known that, even if the primer used is a sequence mismatched with a template nucleic acid molecule, when the 3'-end part of the primer is complementary, reaction of extending a DNA strand from the 3'-end by a DNA polymerase enzyme progresses. On the other hand, the inventors have found that, when the 3'-end is mismatched, reaction of extending a DNA strand from the mismatched 3'-end by a DNA polymerase is only rarely initiated.

The inventors have compared the Tm value of a primer having a nucleotide sequence mismatched with a template nucleic acid molecule at the center with the Tm value of a primer having a nucleotide sequence mismatched with a template nucleic acid molecule at the 5'-end or 3'-end. As a result, the inventors have discovered that the Tm value of a primer mismatched at the center is considerably lower than the Tm value of a primer not mismatched, but the Tm value of a primer mismatched at the 5'-end or 3'-end is slightly lower than but almost the same as the Tm value of a primer not mismatched.

However, the inventors have found that, with regard to the amount of a reaction product by reaction of extending a DNA strand from the 3'-end of a primer that misfit hybridizes with a template nucleic acid molecule by a DNA polymerase enzyme, a reaction product in which a DNA strand is extended can be obtained at a considerable efficiency when the primer is mismatched at the center or the 5'-end, but a reaction product in which a DNA strand is extended cannot be obtained when the primer is mismatched at the 3'-end.

On the other hand, if the primer is mismatched at the center or the primer is mismatched at the 5'-end, the resulting reaction product has a 5'-end with the nucleotide sequence of the mismatched primer. Accordingly, this reaction product derived from the misfit hybridized primer can fully hybridize with a probe complementary to the nucleotide sequence of such a mismatched primer. In addition, the inventors have discovered that the reaction product derived from the primer not mismatched with a template nucleic acid molecule often misfit hybridizes with a probe complementary to the nucleotide sequence of the primer mismatched at the 5'-end or 3'-end.

The inventors have conducted further investigations based on these findings and found that, by constituting a microarray in which a primer DNA mismatched at the 3'-end and a primer DNA not mismatched, bind to the surface of the same carrier in an array manner via a linker connected to the 5'-end, and then carrying out single-strand PCR amplification reaction using an objective complementary single-strand nucleic acid molecule as a template, a reaction product in which a DNA is extended only to the 3'-end of the primer DNA not mismatched can be obtained, and such a reaction product binds only to a specific spot of the microarray on the carrier surface. In addition, the inventors have also discovered that the presence of this reaction product bound to a specific spot of the microarray on the carrier surface can be easily detected by, for example, labeling the product. Further, the inventors have confirmed that, in such single-strand PCR amplification reaction, by appropriately setting conditions of a thermal cycle of the PCR reaction, so that the primer DNA not mismatched, bound to the surface of the carrier, can hybridize with the template single-strand nucleic acid molecule with high probability, and repeating the thermal cycle in a desired number of times, the amount of the target reaction product bound to a specific spot of the microarray is amplified. Based on these findings, the inventors have accomplished the invention of the method for detecting a single nucleotide polymorphism or genetic polymorphism according to a second embodiment of the present invention to which the PCR amplification reaction of the present invention is applied.

Specifically, the method for detecting a single nucleotide polymorphism or genetic polymorphism according to a second embodiment of the present invention is a method comprising detecting a nucleic acid molecule having a specific nucleotide sequence included in a group of genetic nucleic acid molecules having a single nucleotide polymorphism or genetic polymorphism to detect a single nucleotide polymorphism or genetic polymorphism indicated by the nucleic acid molecule, the method for detecting a single nucleotide polymorphism or genetic polymorphism comprising:

selecting multiple variants of nucleic acid probes having nucleotide sequences corresponding to partial nucleotide sequence which indicate a difference of nucleotide sequences with each other from the group of genetic nucleic acid molecules having a single nucleotide polymorphism or genetic polymorphism;

selecting the partial nucleotide sequences from the multiple variants of nucleic acid probes so that at least one of nucleotides indicating a difference with each other in the single nucleotide polymorphism or genetic polymorphism is located on the 3'-end side in the nucleotide sequences of the nucleic acid probes;

constituting a microarray in which the multiple variants of nucleic acid probes bind to the surface of an identical carrier in an array manner via a linker connected to the 5'-end;

carrying out extension of a complementary DNA strand, under conditions in which a nucleic acid molecule having a specific nucleotide sequence to be detected can selectively hybridize with only one of the plurality of nucleotide acid probes constituting the microarray, by PCR amplification reaction using a thermal cycle with the nucleic acid molecule having a specific nucleic acid sequence to be detected as a template and the one of the multiple variants of nucleic acid probes that selectively hybridizes with the template as a primer; and specifying the one of the multiple variants of nucleic acid probes, in which a complementary DNA strand can be extended, in the microarray to detect a single nucleotide polymorphism or genetic polymorphism containing the partial nucleotide sequence corresponding to a nucleotide sequence possessed by the one of the nucleic acid probes specified.

By using the method for PCR amplification reaction according to the first embodiment of the present invention, the time of the thermal cycle spent for PCR amplification reaction used for pretreatment of a sample or preparation of a complementary strand DNA extended to the 3'-end of a primer using a specific single-strand nucleic acid molecule contained in the sample as a template can be significantly reduced.

The method for detecting a single nucleotide polymorphism or genetic polymorphism according to the second embodiment of the present invention can use a single-strand nucleic acid molecule to be detected contained in a sample as a template and allow a single-strand DNA, selectively extended from a primer having a nucleotide sequence complementary to the object to be detected, to bind to a spot of the primer DNA in a microarray on the surface of a carrier via a linker connected to the 5'-end of the primer DNA strand. Accordingly, in principle, the total amount of the reaction product amplified by single-strand PCR can bind to a corresponding spot to carry out detection, and a high detection sensitivity can be achieved. On the other hand, the object to be detected can significantly reduce the total reaction time required for PCR amplification reaction for pretreatment of a sample of preliminarily preparing a DNA strand having a nucleotide sequence the same as that of the template single-strand nucleic acid molecule that hybridizes with the probe while maintaining a large-scale array as in a conventional microarray technology and the subsequent probe hybridization reaction.

In addition, by applying the method for PCR amplification reaction according to the first embodiment of the present invention to the process of PCR amplification reaction when carrying out the method for detecting a single nucleotide polymorphism or genetic polymorphism according to the second embodiment of the present invention, the reaction time can be further reduced.

Other features and advantages of the present invention will be apparent from the following description taken in conjunction with the accompanying drawings, in which like reference characters designate the same or similar parts throughout the figures thereof.

DETAILED DESCRIPTION OF THE PREFERRED EMBODIMENTS

Figure 1:
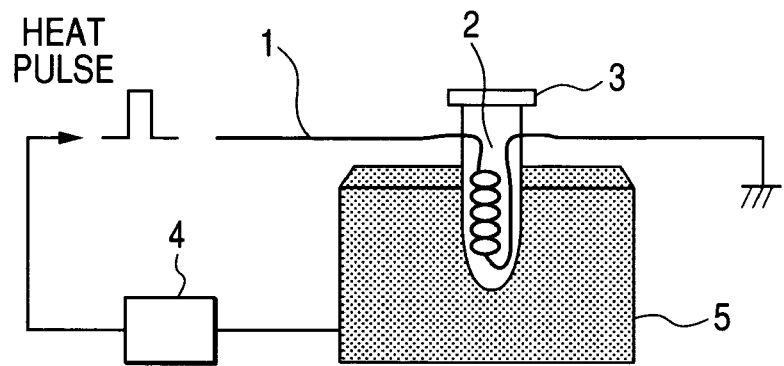
FIG. 1 shows a schematic diagram of a PCR vessel with built-in micro heater and a reaction solution heating method with high responsiveness by applying pulsed voltage to the heater used in the method for PCR amplification reaction according to the first embodiment of the present invention.

Preferred embodiments of the present invention will now be described in detail in accordance with the accompanying drawings.

The present invention will be described in more detail below.

[Method for PCR Amplification Reaction According to the First Embodiment of the Present Invention]

In the method for PCR amplification reaction according to the first embodiment of the present invention, each thermal cycle comprises:

an annealing step of forming a double strand by hybridization of a template single-strand nucleic acid molecule and a primer; or binding to the complementary strand;

an extension step of carrying out reaction of extending a DNA strand from the 3'-end of the primer constituting such a double strand by effecting a DNA polymerase enzyme after the hybridization; and a denaturing step of thermally dissociating the double-strand nucleic acid and separating into single-strand nucleic acid molecules and their complementary strands, wherein the entire reaction vessel is placed on a heating block maintained at the annealing temperature to prewarm the reaction vessel at the annealing temperature, and temporary heating to the extension temperature and to the denaturing temperature is provided by using a heater for local heating attached to the reaction vessel. Applying predetermined pulsed voltages to the heater for local heating to generate thermal pulses and setting up this heater in the form in which the heater will be in direct thermal contact with the reaction solution will increase the temperature of the reaction solution to the extension temperature and to the denaturing temperature at thermal responsiveness of at least millisecond order due to the thermal pulses. In this denaturing step for thermally dissociating the double-strand nucleic acid and separate into single-strand nucleic acid molecules and their complementary strand, most of the double-strands can be thermally dissociated in a heating time of several tens of milliseconds by setting the denaturing temperature high enough. In addition, although the time of the extension step to complete the extension reaction of DNA strands with DNA polymerase enzyme to synthesize the complementary strands, the extension reaction can be sufficiently completed in a extension time of several hundred milliseconds unless the length of nucleic acid to be synthesized in the extension reaction is extremely long. Thus, the time for a single thermal cycle can be shortened to nearly one second by carrying out thermal cycles with an extension step for several hundred milliseconds, a denaturing step for several tens of milliseconds, and an annealing step with applying no voltage to the heater for local heating. Even when the thermal cycle is repeated several tens of times, the total time required for the thermal cycles can be shortened to several tens of seconds to several minutes. In practice, the time for preheating the heating block, and for cooling after the completion of PCR amplification reaction will be also necessary as in conventional PCR methods, the time for the thermal cycles themselves, which are necessary for PCR amplification reaction can be shortened to nearly the limit.

Moreover it was confirmed that the temperature maintained for the heating block is not necessary to be at the annealing temperature, but can be below the annealing temperature. This is because the lower temperatures have, in principle, an advantage for shortening the cooling time, as it apparent in the light of thermal flux, and it is possible to start applying voltage pulses for denaturing when the reaction solution reaches at the annealing temperature before it become the same temperature as the heating block. On the other hand, this has an apparent disadvantage for increasing temperature toward the denaturing temperature. For example, the PCR method of the present invention was possible to maintain the stable sample temperatures with a heating block set at approximately 37° C.

The method for PCR amplification reaction according to the first embodiment of the present invention is a method for PCR amplification reaction comprising amplifying, from a template nucleic acid chain, a DNA strand having a corresponding nucleotide sequence by PCR reaction, the method for PCR amplification reaction comprising:

using, as a reaction vessel for storing a PCR reaction solution containing the nucleic acid chain as a template, a reaction vessel is which a heater is placed at a position at which the heater can thermally contact the stored reaction solution, and the storing capacity of the reaction solution and the shape of the solution storing section are designed in order to exhibit a heat capacity in which the temperature of the reaction solution can respond to the thermal pulse generated by applying a predetermined pulsed voltage to the heater in the order of at least milliseconds;

storing the PCR reaction solution of the designed storing capacity in a solution storing section of the reaction vessel with the heater;

bringing the entire reaction vessel with the heater into contact with a heating block maintained at a predetermined temperature to maintain the vessel at the predetermined temperature in a continuous manner;

applying a predetermined pulsed voltage to the heater provided in the reaction vessel and carrying out pulsed heating corresponding to the pulse time width and the pulse voltage height to from a thermal cycle for PCR reaction; and providing a step of carrying out PCR reaction by repeating application of the pulsed voltage a plurality of times and correspondingly repeating the thermal cycle a plurality of times. In the first embodiment, the invention also provides a PCR reaction apparatus and a PCR reaction vessel used in the method for PCR amplification reaction according to the first embodiment of the present invention.

Thus, the PCR reaction apparatus according to the first embodiment of the present invention is a PCR reaction apparatus having the above configuration in which PCR reaction can be carried out in accordance with the method for PCR amplification reaction according to the first embodiment of the present invention, the PCR reaction apparatus by comprising:

a reaction vessel used as a reaction vessel for storing a PCR reaction solution, a heater is placed at a position at which the heater can thermally contact the stored reaction solution directly, and the storing capacity of the reaction solution and the shape of the solution storing section are designed in order to exhibit a heat capacity in which the temperature of the reaction solution can respond to the thermal pulse generated by applying a predetermined pulsed voltage to the heater in the order of at least milliseconds;

a heating block that has a structure in which the reaction vessel with the heater can be held, and can maintain the entire reaction vessel at a predetermined temperature in a continuous manner through thermal conduction by bringing the reaction vessel into therewith;

a heating block temperature control mechanism for controlling the temperature of the heating block at a predetermined temperature;

a pulsed voltage generating mechanism for applying a pulsed voltage with a desired pulse time width and a desired pulse voltage height to the heater placed in the reaction vessel a desired number or times periodically;

an MPU unit for managing the operation of the heating block temperature control mechanism and the pulsed voltage generating mechanism;

a key input device for inputting and setting the managing conditions of the MPU unit; and a display for displaying the managing conditions of the MPU unit or the managed status information.

The PCR reaction vessel according to the first embodiment of the present invention is a PCR reaction vessel having the above configuration in which PCR reaction can be carried out in accordance with the method for PCR amplification reaction according to the first embodiment of the present invention, the reaction vessel for storing a PCR reaction solution being a reaction vessel with a heater, a heater is placed at a position at which the heater can thermally contact the stored reaction solution directly, and the storing capacity of the reaction solution and the shape of the solution storing section are designed in order to exhibit a heat capacity in which the temperature of the reaction solution can respond to the thermal pulse generated by applying a predetermined pulsed voltage to the heater in the order of at least milliseconds.

(Forms of the Heater and the Reaction Vessel)

Figure 2:
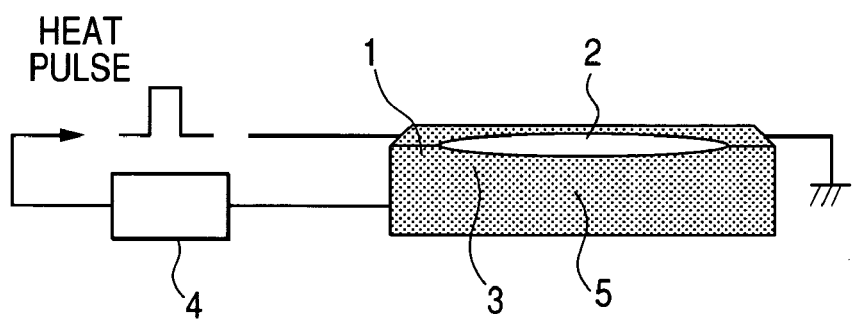
FIG. 2 shows a schematic diagram of a PCR vessel with a seat form heater and a reaction solution heating method with high responsiveness by applying pulsed voltage to the seat form heater used in the method for PCR amplification reaction according to the first embodiment of the present invention.

FIGS. 1 and 2 show a typical embodiment of the PCR reaction vessel according to the first embodiment of the present invention.

FIG. 1 shows an example of a PCR reaction vessel of a conventional capillary form in which a coiled heater 1 is configured to have direct contact with the reaction solution. For this built-in coiled heater 1, for example, a nichrome wire heater (several tens to several hundred ohms) may be used and thermal pulses generated by applying a pulsed current (pulsed voltage) to the heater is provided to a PCR reaction solution 2 in a PCR reaction vessel 3. As a result, PCR reaction solution 2 receives local heating according to calories of the thermal pulses with a desired interval time. Since the entire capillary PCR vessel is maintained in a heating block 5 made from material with a large thermal capacity and a high thermal conductivity, heat is then diffused via thermal conduction to heating block 5. The heating block 5 is maintained at the annealing temperature and local pulsed heating corresponding to an extension step of several hundred milliseconds and a denaturing step of several tens of milliseconds is provided using the built-in coiled heater 1 described above. PCR amplification reaction can be performed by repeating this thermal cycle.

FIG. 2 shows an example where a solution storing section for retaining reaction solution itself is formed in a plate shape. Particularly, the bottom of the solution storing section utilizes surface of a sheet-form heat layer 1 and the sidewall thereof utilizes a recessed part of heat radiation silicone rubber sheet 3. Though reaction solution 2 maintained in this solution storing section has a thin insulating layer, it has a direct thermal contact with the surface of the sheet-form heater layer 1, which forms the bottom. Therefore, the thermal pulses generated in the sheet-form heater layer 1 are provided directly, and the PCR reaction solution 2 receives a local heating according to calories of the thermal pulses with a desired interval time. The sidewall of the solution storing section is formed with heat radiation silicone rubber sheet 3, and the sheet-form heater layer 1, which forms the bottom, is formed in close contact with the underlying heat block 5, allowing heat dissipation by thermal conduction to heat radiation silicone rubber sheet 3 and to heating block 5 after heating.

Preferably the form of the entire reaction vessel is in a sealable structure with a lid to prevent the evaporation of water contained in the reaction solution during PCR reaction.

On the other hand, as a local heat source for the reaction solution a heater is built in or attached to the reaction vessel. For this, the setting position of the heater is to be chosen so that the heat generated by the heater can be transferred promptly to the reaction solution. Therefore, the heater is preferably in a form in which a large contact area can be attained.

A large contact area can be attained in a form of nichrome wire heater that is made as fine as possible in a coil shape and placed in a small vessel as shown in FIG. 1, or in a form of thin film heater layer placed as a plane at the bottom of a liquid vessel with a liquid layer that is as thin as possible as shown in FIG. 2. Also, calories provided to the PCR liquid in contact with the surface of a heater increase the temperature of the entire liquid in the PCR liquid by the thermodiffusion process. Therefore, even when a large contact area between the heater and the reaction solution is attained, there will be a significant delay in increasing temperature in parts of the solution that is too far from the heater. Thus, it is preferable that the storing capacity and the vessel shape for a reaction solution within a PCR vessel have a heat capacity that enables the reaction solution to respond in solution temperature in time of millisecond order, and that solution thickness of the reaction solution from the surface of the heater is limited. Particularly, since it can be assumed that thermal and physical property values of a PCR reaction solution are nearly equal to water, and the thermal diffusivity a in a thermal conduction process is defined by the thermal conductivity $\lambda$, the thermal capacity Cp, and the density of material $\rho$ as in $$a=\lambda/(Cp\cdot\rho)(m^2/s),$$

the thermal diffusivity a is calculated as 0.143 mm$^2$/s by assigning the thermal capacity Cp of water (specific heat): 1 Cal/deg·g, the heat conductivity $\lambda$:0.001429 cal/cm·s·deg, and the density $\rho$:1 g/cm$^3$ in this relation. Since root 0.143 is approximately 0.38, when considering one dimensional thermal diffusivity only, calorie diffusion to the entire reaction solution can be attained in a second with a reaction solution of approximately 0.38 mm in solution thickness or with a reaction solution of approximately this thickness between heaters in a capillary. Also in the case of providing multiple pulses with a controlled duty ratio, the time constant in a thermal response of the entire reaction solution can be estimated approximately in reference to this value.

The material of a reaction vessel itself cane be also chosen for appropriate thermodiffusion properties by calculating the time constant in the process of getting cooled after providing thermal pulses with the assignment of its physical property values. In a method for PCR amplification reaction according to the first embodiment of the present invention, a reaction vessel is hardly a problem since the entire reaction vessel only needs to be cooled down to the annealing temperature by the end of the annealing step by maintaining the outer heating block 5 itself at the annealing temperature. However when using a vessel of polymeric material, such as plastic, the ratio of heat conductivity $\lambda$/thermal capacity Cp (specific heat) may be as small as water. In this case it is preferable that the thickness of the reaction vessel itself is equal to or smaller than the above thickness or a vessel not too thick is preferable.

(Forms of Applied Current Pulses)

Thermal cycles in a PCR reaction are usually composed of repeating cycles of solution temperature changes among a denaturing step, an annealing step and an extension step in this order. The temperature of an extension step is set between the denaturing temperature and the annealing temperature. Optionally the temperatures of an extension step and an annealing step can be set at the same temperature, and in this case thermal cycles repeat cycles of solution temperature changes between a denaturing temperature and an annealing temperature in this order.

For example, increasing the length of a primer sequence, which is usually approximately 20 mer with an extension temperature of 72° C., increases the Tm of the primer and allows to perform PCR reaction in the conditions closer to the denaturing temperature. This provides an advantage for accelerating thermal cycles as it is not necessary to reduce Tm to the annealing temperature, which is usually 55 to 60° C. with approximately 20 mer of primers. For example, the high speed PCR of the present invention is also possible with a system in which a primer is designed longer to have a Tm of 76° C. and temperature is changed between 76° C. and the denaturing temperature.

In the method for PCR amplification reaction according to the first embodiment of the present invention, an outer heating block 5 itself is maintained at an annealing temperature and an entire reaction vessel is preheated to this annealing temperature. During the time of an extension temperature and a denaturing temperature, which are chosen to be higher temperature than the annealing temperature pulsed voltage is applied to a heater to generate thermal pulses.

Figure 6:
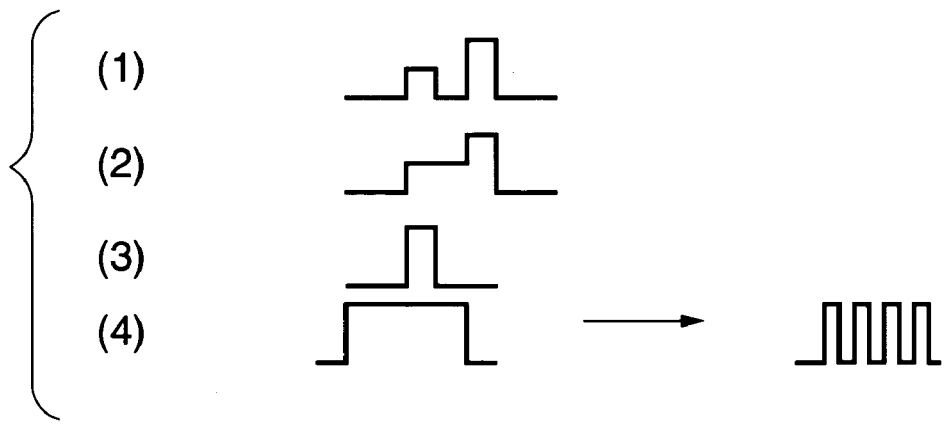
FIG. 6 shows a schematic diagram of examples of forms of pulsed voltage applied to a heater for local heating used in the method for PCR amplification reaction according to the first embodiment of the present invention.

FIG. 6 shows examples of pulsed voltage forms applied between both ends of a heater wire to provide pulsed current to this heater. In FIG. 6, (1) and (2) correspond to thermal cycles with 3 steps of an annealing temperature, an extension temperature and a denaturing temperature. Since an extension temperature is set at a temperature higher than the annealing temperature and lower than the denaturing temperature, a pulse of a lower wave height for extension and a following pulse at higher in the wave height for denaturing are applied after an annealing steps. After applying this pulse for denaturing, the solution temperature, which has once increased, decreases again to the annealing temperature by thermal diffusivity to an outer heating block.

In FIG. 6, (3) corresponds to the case in which an annealing temperature and an extension temperature are chosen to be the same temperature. Double-strand nucleic acid is dissociated into single stranded chains by applying a pulse with a high wave height for denaturing. Then, the solution temperature decreases gradually to the annealing temperature, and primer molecules hybridize with template single stranded nucleic acid molecules followed by extension of complementary DNA strands at the 3'-ends of primer molecules with DNA polymerase enzyme to produce double-strand nucleic acid.

In addition, instead of using a single pulse current to control its current magnitude in (3), a format in which a row of current pulses of a sufficiently narrow pulse width and a higher pulse height is used and by controlling its duty ratio the solution temperature, which is averaged among the pulses, is maintained at the desired denaturing temperature can be chosen. Thus, based on the storing capacity and the vessel shape for reaction solution within a PCR vessel to be used the solution temperature, which is averaged when using a row of pulsed current can be estimated based on a predetermined thermal time constant. When using this row of pulsed current with a controlled duty ratio, the overshoot phenomenon, in which local temperature excesses a target temperature in great deal, can be avoided even in the cases the phenomenon occur with a single pulse current.

(Overall Structure of PCR Reaction Apparatus)

Figure 3:
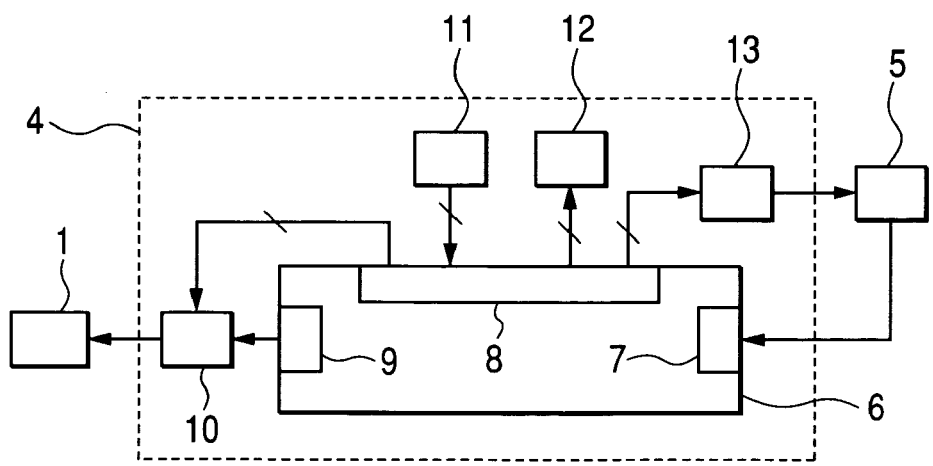
FIG. 3 shows a schematic diagram of the structure of an MPU unit 4 that serves for applying pulsed voltage to a heater for local heating 1, and heating a heating block 5 and controlling the temperature thereof, used in the method for PCR amplification reaction according to the first embodiment of the present invention.

In a brief description the PCR reaction apparatus comprises a heating block 5, which has a structure for retaining PCR reaction vessel 3 with a built-in heater 1 in the above description, signal generating means for providing pulsed current to the heater 1, and an MPU unit 4 with a mechanism of controlling temperature of heating block 5. FIG. 3 shows the internal structure of an MPU unit 4. A single-chip microcomputer 6 contains an analog input 7 with built-in A/D converter, an I/O port 8 of digital input/output, and a timer counter port 9 to generate a chosen pulse sequence. The generated chosen pulse sequence is input to a current driver circuit 10. The current driver circuit 10 contains a multi selector from the I/O port 8 of digital input/output, and can choose one of several preset values for wave height to apply pulsed current (apply pulsed voltage) to the heater 1. The MPU unit 4 also comprises a display 12 to inform of states etc. of the device and a key input device 11 to instruct a pulse sequence. The data of such information can be stored in'the memory in the single-chip microcomputer 6. A Peltier driver circuit 13 for preheating and setting the outer heating block 5 at the base annealing temperature is connected to the I/O port 8 of digital input/output, and temperature information from the Peltier device and a built-in temperature sensor incorporated in the heating block 5 is input into the analog input 7 and used for feeding back of the temperature control.

Execution of temperature cycling in PCR reaction may be started in a format in which an experimenter push a start button for a program for a pulse sequence. On the other hand, in a method for PCR amplification reaction according to the first embodiment of the present invention, the time required for temperature cycling used in PCR reaction may be approximately tens of seconds. In such a case, the start may be in a format in which after preprogramming all the thermal processes including the preheating by the heating block 5, for example, the time of completing the connection of the heater 1 after placing the heat vessel 3 with the built-in heater 1 on the heating block 5 is confirmed by detecting the heater resistance to start the program automatically.

As described in the foregoing, the time required for PCR amplification reaction with as many times of thermal cycle as conventional methods can be shorteneded to several tens of seconds by applying a method for the PCR amplification reaction according to the first embodiment of the invention. Moreover, by shortening the time required for each temperature cycling, the time for the heat resistant polymerase enzyme used in PCR amplification reaction to be exposed to height temperature is also shortened. Therefore, thermal deterioration of the heat resistant polymerase enzyme during PCR amplification reaction can be reduced in great deal thereby providing efficient means for maintaining its activity.

In addition, the bottom of the plate form of reaction vessel illustrated in FIG. 2 and described above can be made in a similar form to commercially available slide glasses for microscopes. Therefore by immobilizing nucleic acid probes in arrays on the surface of the insulating layer for the heater layer attached to the surface of the reaction vessel, the reaction vessel becomes a PCR vessel with DNA microarrays on the surface of the bottom. The PCR vessel with DNA microarrays in this aspect is preferably available in carrying out a method for detecting single nucleotide polymorphism or genetic polymorphism according to the second embodiment of the present invention.

[A method for Detecting Single Nucleotide Polymorphism or Genetic Polymorphism According to the Second Embodiment of the Present Invention]

The method for detecting a single nucleotide polymorphism or genetic polymorphism according to the second embodiment of the present invention is a method for detecting nucleic acid with specific nucleotide sequence selectively among multiple variants of nucleic acid molecules showing single nucleotide polymorphism or genetic polymorphism by using PCR amplification reaction.

Generally, conventional methods comprise preparing DNA strands corresponding to the nucleotide sequences beforehand as PCR products by performing PCR amplification reaction using multiple variants of nucleic acid molecules showing single nucleotide polymorphism or genetic polymorphism in the primary sample as templates; and detecting polymorphism in these PCR products using probes having specific sequences for each single nucleotide polymorphism or genetic polymorphism. On the other hand the method for detecting a single nucleotide polymorphism or genetic polymorphism according to the second embodiment of the present invention utilizes DNA primers with specific sequences for each single nucleotide polymorphism or genetic polymorphism, and detects the products that has extended DNA strands selectively in single chain PCR amplification reaction using as templates those with corresponding nucleotide sequences among multiple variants of nucleic acid molecules showing single nucleotide polymorphism or genetic polymorphism in the primary sample. In this method, the DNA primers themselves to be used are immobilized on the surface of carrier before the reaction to allow an efficient detection of amplified products that has extended DNA strand selectively.

The method for detecting a single nucleotide polymorphism or genetic polymorphism according to the second embodiment of the present invention utilizes DNA prove microarrays where multiple variants of nucleic acid probes with specific sequences for each single nucleotide polymorphism or genetic polymorphism are immobilized in arrays on the surface of the same carrier as in detection methods using conventional microarray technology. Any of these multiple variants of nucleic acid probes is immobilized on the surface of a carrier at its 5'-end via a linker and prepared in a form that allows hybridization with single stranded nucleic acid molecules with the corresponding nucleotide sequences. On the other hand, each nucleic acid probe is chosen to have a sequence that has a perfect match to one of the multiple variants of nucleic acid molecules showing single nucleotide polymorphism or genetic polymorphism, and nucleotide sequence mismatches to the other variants, particularly on the 3'-end side thereof with at least one mismatch. Therefore a nucleic acid probes extends a complementary DNA strand at the 3'-end of the nucleic acid probe using a full-matched single stranded nucleic acid molecule as template with DNA polymerase enzyme after hybridizing with a full matched single stranded nucleic acid molecule, On the other hand with a single stranded nucleic acid molecule a nucleic acid probe may be involved in misfit hybridization, the extension of DNA strand at the 3'-end of the nucleic acid probe will not occur in principle due to the presence of a mismatch base at least in its 3'-end even when DNA polymerase is used to the double-strand part. As a result, among the nucleic acid probes immobilized in arrays on the surface of a carrier, only the nucleic acid probes that can have a full-match hybridization to a single stranded nucleic acid molecule in the primary sample can extend a complementary DNA strand at its 3'-end. By detecting spots of nucleic acid probe that have extend a DNA strand, single stranded molecules in the primary sample are identified. This extension reaction of DNA strands uses PCR reaction with nucleic acid probes immobilized on the surface of a carrier via a linker as primers, and the entire detection time can be shortened in a great deal by employing the method for PCR amplification reaction according to the first embodiment of the present invention described above.

The method for detecting a single nucleotide polymorphism or genetic polymorphism according to the second embodiment of the present invention is a method comprising detecting a nucleic acid molecule having a specific nucleotide sequence included in a group of genetic nucleic acid molecules having single nucleotide polymorphism or genetic polymorphism to detect a single nucleotide polymorphism or genetic polymorphism indicated by the nucleic acid molecule, the method for detecting a single nucleotide polymorphism on genetic polymorphism comprising:

selecting multiple variants of nucleic acid probes having nucleotide sequences corresponding to partial nucleic sequences which indicate the difference of nucleotide sequences with each other from the group of genetic nucleic acid molecules of genes having a single nucleotide polymorphism or genetic polymorphism;

selecting the partial nucleotide sequences from the multiple variants of nucleic acid probes so that at least one of nucleotides indicating a difference with each other in the single nucleotide polymorphism or genetic polymorphism is located on the 3'-end side in the nucleotide sequences of the nucleic acid probes;

constituting a microarray in which the multiple variants of nucleic acid probes bind to the surface of an identical carrier in an array manner via a linker attached to the 5'-end of the probes;

carrying out extension of a complementary DNA strand, under the conditions in which a nucleic acid molecule with a specific nucleotide sequence to be detected can selectively hybridize with only one of the multiple variants of nucleic acid probes constituting the microarray, by PCR amplification reaction using a thermal cycle with the nucleic acid molecule having a specific nucleic acid sequence to be detected as template and the one of the multiple variants of nucleic acid probes that selectively hybridizes with the template as primer among; and specifying the one of the multiple variants of nucleic acid probes in which a complementary DNA strand can be extended, in the microarrays to detect a single nucleotide polymorphism or genetic polymorphism containing a partial sequence corresponding to the nucleotide sequence possessed by the one of the multiple variants of nucleic acid probes specified wherein it is possible and preferable to have a thermal cycle with a denaturing step, an annealing step and an extension step, and to set the time for any of the denaturing, annealing and the extension steps not longer than 10 seconds.

Additionally, the second embodiment of the present invention also provides a reaction vessel that can be used in the step of PCR amplification reaction in the method for detecting a single nucleotide polymorphism or genetic polymorphism according to the second embodiment of the present invention.

Thus, the reaction vessel for detecting a single nucleotide polymorphism or genetic polymorphism according to the second embodiment of the present invention is a reaction vessel for detecting a single nucleotide polymorphism or genetic polymorphism having the above configuration, in which PCR amplification reaction for detecting a single nucleotide polymorphism or genetic polymorphism can be carried out in accordance with the method for detecting a single nucleotide polymorphism or genetic polymorphism according to the second embodiment of the present invention, wherein the detection of an objective single nucleotide polymorphism or genetic polymorphism means detection of a nucleic acid molecule having a specific nucleotide sequence included in a group of genetic nucleic acid molecules having a single nucleotide polymorphism or genetic polymorphism to detect a single nucleotide polymorphism or genetic polymorphism indicated by the nucleic acid molecule;

multiple variants of nucleic acid probes having nucleotide sequences corresponding to partial nucleic sequences which indicate a difference of nucleotide sequences with each other in nucleotide sequence are selected from the group of genetic nucleic acid molecules having a single nucleotide polymorphism or genetic polymorphism;

the partial nucleotide sequences are selected from the multiple variants of nucleic acid probes so that at least one of nucleotides indicating a difference with each other in the single nucleotide polymorphism or genetic polymorphism is located on the 3' side in the nucleotide sequences of the nucleic acid probes;

a microarray is provided so that the plurality of nucleic acid probes bind to the surface of an identical carrier in an array manner via a linker connected to the 5'-end of the probe, the carrier constituting the microarray is placed in the reaction vessel so that the surface of the carrier can be brought into contact with a reaction solution in the reaction vessel, and the multiple variants of nucleic acid probes constituting the microarray on the surface of the carrier can thermally contact a heat source forming a temperature change of a thermal cycle in the PCR amplification reaction via thermal conduction in the carrier; and the storing capacity of a reaction solution and the shape of a solution storing section in the reaction vessel are designed so that, in the PCR amplification reaction, the solution thickness of the reaction solution in contact with the multiple variants of nucleic acid probes is 3 mm or less in the normal direction with respect to the surface of the carrier to which the multiple variants of nucleic acid probes bind. Moreover, an inorganic material is preferred as a material for the carrier having a surface to which the multiple variants of nucleic acid probes constituting the microarray binds in this reaction vessel.

In the method for detecting a single nucleotide polymorphism or genetic polymorphism according to the second embodiment of the present invention, nucleic acid probes used in the detection can be in a format of DNA probe microarrays in which multiple variants of nucleic acid probes with specific nucleotide sequence for each single nucleotide polymorphism or genetic polymorphism are immobilized in arrays on the same carrier as in the detection methods using conventional microarray technology. Therefore, the present invention has an advantage of being capable of composing arrays in a large scale even with large numbers of different nucleic acid probes, as a characteristic of microarray technology.

On the other hand, the PCR amplification reaction used in the detection step uses the nucleic acid probes that are linked to the same carrier surface via linker at the 5'-end as PCR primers. Therefore, for the reaction solution used in this PCR amplification reaction step the solution thickness covering the surface of the microarrays is not necessary to be thick more than needed. In other words, in PCR amplification reaction process the solution thickness covering the surface of the microarrays may be as thin as approximately 0.1 mm when evaporation of the reaction solution is prevented. At least, in the detection method of the present invention, the solution thickness of the reaction solution for PCR amplification reaction on microarrays can be selected in the range of 3 mm or less, and preferably in the range of 1 mm or less.

With a PCR reaction apparatus using capillary vessels, the time to complete thermal cycles in PCR can be shortended, for example, to ½ to ⅓ of conventional methods by using glass capillary vessels with an superior heat conductivity to resin vessels and increasing the rate of temperature changes upon heating and cooling in thermal cycles such as Roche Light Cycler. Moreover, SCIENCE, Vol. 280, 15 MAY 1998, has reported that a desired amplification rate has been achieved with thermal cycles of 90 seconds at max in PCR amplification reaction similarly using capillaries with small heat capacity.

Similarly, in the method for detecting single nucleotide polymorphism or genetic polymorphism in the PCR amplification reaction process thermal cycles in PCR can be shortenened in greatly by reducing the solution thickness of the reaction solution covering the surface of microarrays, and using a material with superior heat conductivity, such as glass, for the carrier for microarrays with providing heating and cooling of reaction solution by the carrier. Particularly, it is possible to complete thermal cycles in PCR amplification process on the microarrays in several tens of seconds by applying the method for PCR amplification reaction according to the first embodiment of the present invention as descried above. In this case, for example with the plate form of PCR reaction vessel illustrated in FIG. 2, the insulating layer, for example a $SiO_2$ layer, on the surface of the heater layer used as the bottom, can be used as a carrier surface for microarrays.

In the detection methods using conventional microarray technology, nucleic acid molecules in the primary sample is subjected to a pretreatment to amplify DNA strands with the corresponding nucleotide sequences by performing PCR amplification reaction using reaction vessels made or resin. Then the amplified product DNA strands of detection targets are immobilized on the spot points of corresponding nucleic acid probes by hybridization between amplified product DNA strands prepare by the pretreatment and nucleic acid probes on microarrays. On the other hand the method for detecting single nucleotide polymorphism or genetic polymorphism utilizes nucleic acid probes immobilized on microarrays as PCR primers, and conduct a direct detection by single-strand PCR amplification reaction to lead the extension of DNA strands at 3'-end of the nucleic acid probes. Therefore, at least the hybridization reaction in the later step is not necessary in the detection method of the present invention, contributing to the reduction in the detection time.

Figure 8:
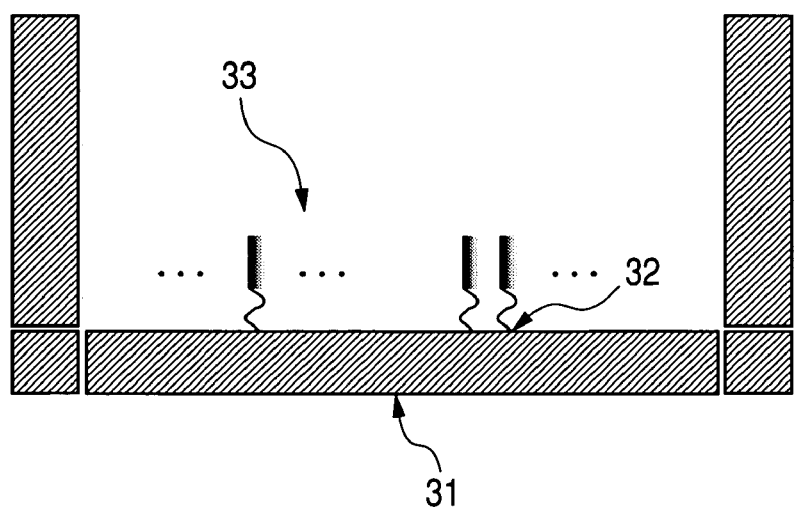
FIG. 8 shows a schematic diagram of a PCR amplification reaction vessel with, on the bottom, microarrays of nucleic acid probes used in the detection method of SNPs and genetic polymorphisms according to the second embodiment of the present invention.

FIG. 8 shows an example of an embodiment of the reaction vessel for detecting a single nucleotide polymorphism or genetic polymorphism according to the second embodiment of the present invention. In this reaction vessel a carrier for microarrays 31 is placed at the bottom and also serves as the bottom. Nucleic acid probes 33 are linked to the surface of this carrier for microarrays 31 at the 5'-end thereof via a linker 32 in arrays on the predetermined spot points on the surface of the carrier to compose microarrays. Reaction solution is injected into the reaction vessel to cover the surface of these microarrays and subjected to PCR amplification reaction. In the reaction the solution thickness of the reaction solution is chosen to be shorter than 3 mm, which is sufficiently short compared to the size of plane face of the vessel, and heating and cooling of the reaction solution is mainly provided by thermal conduction via the bottom carrier for microarrays 31. Therefore a material with a superior heat conductivity λ and superior heat dissipation a defined by the following expression is preferably used as a material for the carrier for microarrays 31. In the thermal conduction process, the heat dissipation a is defined by the following expressions by using thermal conductivity λ, thermal capacity Cp, and the density ρ of the material.

$$a=\lambda/(Cp\cdot\rho)(m^2/s)$$

In conventional microarray technology, slide glass etc. have been used as carrier for DNA microarray. Though thermal conductivity of fused silica is high when compared to usual glasses, it is one order lower than thermal conductivity of crystalline silicon, and approximately two orders lower than thermal conductivity of metals. Crystalline silicon and metallic material are preferred as a major constituent material for a carrier for microarrays 31 when providing cooling and heating with a heat source and an external heat sink under a carrier for microarrays 31. Moreover the total heat capacity of a carrier for microarrays 31 is in proportion to the thickness of the carrier and the reopens rates of thermal conduction to and from a heat source and an external heat sink are also dependent on the thickness of the carrier. Therefore, a thinner carrier is preferable as long as it retains in the range of sufficient mechanical strength for handling of the entire reaction vessel. For example, rectangular silicon wafer in a form of a slide glass can be handled without problems with thickness of several hundred microns.

Heat capacity Cp and density of material $\rho$ are unique physical property values of materials. Taken them into consideration with calculations of heat dissipation a, inorganic materials are generally more preferable than organic polymer compound such as plastic. Crystalline inorganic materials are more preferred when compared with inorganic amorphous material of the same material. For example, in the second embodiment of the present invention, glass, silicon wafer, and aluminum, etc. can be used for a carrier for microarrays and they are also economically advantageous in producing cost. It is also possible to use glass and silicon wafer as a substrate and have a metal film, such as, gold, platinum, and silver on the silicon wafer on the surface of microarray forming part for improving temperature homogeneity in the area. Moreover the equipment of metal film on the surface of microarray forming part provides easier immobilization of nucleic acid probes via a linker at the 5'-end by pre-introducing sulfonyl group (SH group) to the linker. Nucleophilic of sulfonyl group (SH group) can be used to provide binding of the linker end to metallic atoms for easier immobilization.

To silicon wafer and $SiO_2$ film (including glass) a reactive functional group available for binding formation is introduced by pretreating the surface with a silane coupling agent. Using the introduced functional group on the surface, a covalent bond with the linker at the 5'-end of nucleic acid probes can be formed for the immobilization.

Moreover, similar to the PCR amplification reaction vessel according to the first embodiment of the present invention shown in FIG. 2 and descried above, a heater layer, which is available for a heater for local heating, can be installed on the surface of rectangular silicon wafer forming the bottom of this reaction vessel. The surface of the heater layer is covered with a $SiO_2$ film as an insulating layer, and available as a carrier surface for immobilizing a linker attached to the 5'-end of nucleic acid probes. This allows direct heating of the reaction solution by applying current to the installed heater layer. Thus, as described above, generation of thermal pulses become possible by applying pulsed current to the installed heater layer only for denaturing steps and extension steps in thermal cycles in PCR reaction. As a result, with a solution thickness of approximately 0.3 mm, one thermal cycle can be set at approximately 1 second to perform PCR reaction, and with a solution thickness of 3 mm or less, step response times can be set at approximately several seconds to perform PCR reaction.

In such reaction, cooling after a pulsed heating is mediated by heat dissipation through the carrier, inorganic materials, including glass, have one order greater thermal diffusivity rate a than water, thereby providing rapid dissipation. However organic polymer materials, such as plastic, have equivalent thermal diffusivity rates a, and with a thick carrier responsiveness in cooling become significantly decreased.

When a layer of reaction solution is thin the reaction solution may be excessively concentrated by evaporation of water from the surface of the liquid upon heating in PCR reaction. As prevention measure, the reaction vessel is preferable to have a structure to seal the solution storing section with a lid when using a reaction solution of thin layer. Preferably the solution storing section itself has a small chamber volume to reduce the amount of vapor from the reaction solution in the sealed liquid vessel.

In the second embodiment of the present invention, PCR amplification reaction proceeds on the surface of a microarray, and for example, substrates of DNA polymerase enzyme near the surface thereof are consumed. Particularly, when the substrates of the enzyme are consumed in the neighboring spots on the surface of a microarray, reaction rate may locally decrease. From this point of view, when the solution thickness of the reaction solution is small, it is desirable to agitate the reaction solution. For example, PCR equipment implemented with agitation function such as vortex mixer, shaker, etc. meets this purpose. When commercially available heating block type PCR equipment is used, it is generally desirable to use heating blocks with small heat capacity so that the temperature follow-up of the heating blocks for heating sources themselves may be enhanced. It is also possible to enhance the temperature follow-up by using a commercial Peltier element and a commercial Peltier temperature controller in combination as a heating source.

Furthermore, if each thermal cycle can be carried out at a high speed, the time period during which the DNA polymerase enzyme used for PCR reaction, for example, Taq DNA polymerase enzyme is exposed to high temperature will be short. Accordingly, on the contrary to the time period needed in the conventional thermal cycle, in which it has been found that the enzyme activity decreases when the number of repetition exceeds 40 times, it is possible to increase the number of repetition to about 100 times while avoiding the decrease in the enzyme activity by shortening the time needed for each thermal cycle. By making use of this advantage, the total amount of the nucleic acid probe for the extension of the target DNA strand will be sufficient for satisfying the detection sensitivity even by single-strand PCR amplification reaction alone in which nucleic acid probes immobilized on the carrier surface are used as primers.

That is, in the conventional pretreatment, although the number of the repeating times has limitations, total amplification efficiency is enhanced by simultaneously amplifying the both of the double-stranded DNA. Then, the total amount of DNA strand which is immobilized by hybridization and extends on the spot on the microarray is made sufficient for attaining the required detection sensitivity by enhancing the initial amplification efficiency although the efficiency of hybridization with the nucleic acid probe on the microarray is not necessarily high. In the second embodiment of the present invention, although there is no improvement in the amplification efficiency itself when using single-strand PCR amplification reaction, the number of repetition is increased and the extended DNA strands are connected with the nucleic acid probes. As a result, it is immobilized on each spot and the total amount of the extended DNA strand to be detected will fall in a range which can attain required detection sensitivity.

Furthermore, according to the method for detecting a single nucleotide polymorphism or genetic polymorphism according to the second embodiment of the present invention, not only an embodiment carrying out single-strand PCR amplification reaction using as primers the nucleic acid probes immobilized on the carrier surface but also an embodiment carrying out multiplex PCR amplification reaction using a primer corresponding to a nucleotide sequence which is common among the nucleic acid molecules of the target single nucleotide polymorphism or genetic polymorphism can be used. That is, a DNA strand which is selectively extended with the 3'-end of the nucleic acid probe immobilized on the carrier surface is used as a template along with a primer which has a common nucleotide sequence and the PCR amplification product of the portion sandwiched between the primers is obtained. The 3'-end of this PCR amplification product is naturally complementary to the 5'-end of the template DNA strand immobilized on the carrier surface, i.e., the nucleotide sequence of the nucleic acid probe. Therefore, these PCR amplification products of the second step effect full-match hybridization with the nucleic acid probe in the subsequent third step thermal cycle, resulting in DNA strands selectively extended with the 3'-end of the nucleic acid probe. This multiplex PCR amplification reaction achieves much higher amplification efficiency than the single-strand PCR amplification reaction, it is more effective when the sample to be analyzed contains a small amount of nucleic acid to be detected.

In addition, two or more primers can be put into the sample, for example, when the array is a large-scale array and the polymorphism spans two or more exons. Furthermore, the amount of the immobilized nucleic acid probe and the primer put into the sample side may be in an arrangement of asymmetrical PCR.

In any case, some nucleotides are positioned on the 3'-end of the used nucleic acid probe mismatched with the nucleic acid molecules of the other single nucleotide polymorphism or genetic polymorphism but is matched with the nucleic acid molecule of the target single nucleotide polymorphism or genetic polymorphism and a resulting phenomenon in which only extension of the DNA strand which uses as a template the nucleic acid molecule of the target single nucleotide polymorphism or genetic polymorphism takes place selectively is used. Therefore, even if only one different nucleotide is present in single nucleotide polymorphism (SNP), it can be detected by applying the method for detecting a single nucleotide polymorphism or genetic polymorphism of the second embodiment of the present invention.

On the other hand, according to the conventional method, misfit hybridization occurs at a certain frequency when hybridization of a nucleic acid probe and a DNA strand amplified beforehand is performed in the case of containing an only single mismatch nucleotide. In order to effect distinction between these with regard to the target single nucleotide polymorphism (SNP), the target nucleic acid probe and the other three nucleic acid probes having a mutation in the corresponding nucleotide sequence are spotted respectively, and the amount of the DNA strand fixed to the spot where the full-match hybridization occurs and those fixed to the three other spots where the misfit hybridization occurs should be compared to identify the spot where the full-match hybridization occurs. Particularly when there was no significant difference in the Tm value between the full-match hybridization and misfit hybridization, the judgment thereof required skill.

On the contrary, according to the method for detecting a single nucleotide polymorphism or genetic polymorphism according to the second embodiment according to the present invention, extension of a DNA strand takes place selectively only in one of them for the target single nucleotide polymorphisms (SNP), the judgment thereof can be performed with high accuracy. That is, it can be uniquely determined with high accuracy which nucleotide of A, T, G and C the detected nucleic acid molecule has in the target single nucleotide polymorphism (SNP).

In addition, when hybridization of a nucleic acid probe and a DNA strand amplified beforehand is performed in the conventional method, background may become high in connection with the phenomenon in which DNA strands physically extended on the carrier surface of a microarray may cause adsorption. In order to prevent such an influence, there are not a few cases where additional treatments are needed such as blocking treatment and UV-succinic anhydride treatment. On the contrary, according to the method for detecting a single nucleotide polymorphism or genetic polymorphism of the second embodiment according to the present invention, when the single-strand PCR amplification reaction is used, there are only nucleic acid molecules which exist in the original sample other than the DNA strand extended at the 3'-end of the nucleic acid probe to be detected, and the quantity thereof is too little to pose a problem. In addition, since the DNA strand extended at the 3'-end of the nucleic acid probe to be detected is not firmly bound onto the carrier surface, effective removal of the physically adsorbed nucleic acid molecules can be achieved by performing sufficient washing.

Furthermore, when multiplex PCR amplification reaction is used, in addition to the DNA strand extended at the 3'-end of the nucleic acid probe to be detected the complementary DNA strand also exists but the most of them can be removed by performing washing after carrying out denaturing treatment after PCR amplification reaction. Alternatively, treatment at a proper temperature may be performed to the contrary to allow the DNA strand extended at the 3'-end of the nucleic acid probe to be detected and a complementary DNA strand to form a double-stranded DNA. In any case, it is possible to avoid the problem that background may become high in connection with the phenomenon in which DNA strands physically extended on the carrier surface of a microarray may cause adsorption.

According to the method for detecting a single nucleotide polymorphism or genetic polymorphism of the second embodiment according to the present invention, when single-strand PCR amplification reaction is used, the DNA strand extended at the 3'-end of the nucleic acid probe to be detected is labeled a sign is given to perform detection. For example, radioisotope-labeled dNTP can be used as a, substrate to effect radioisotope-labeling. Alternatively, in the single-strand PCR amplification reaction carried out with a reaction solution to which are added Taq DNA polymerase enzyme and dNTP as a substrate and Dye terminator, the extension of the DNA strand extended at the 3'-end of the nucleic acid probe to be detected terminates when the Dye terminator is taken in at the 3'-end. That is, although the DNA strands extended at the 3'-end of the nucleic acid probe obtained by the single-strand PCR amplification reaction have various DNA strand length, each of them has a 3'-end terminated with Dye terminator.

Figure 9:
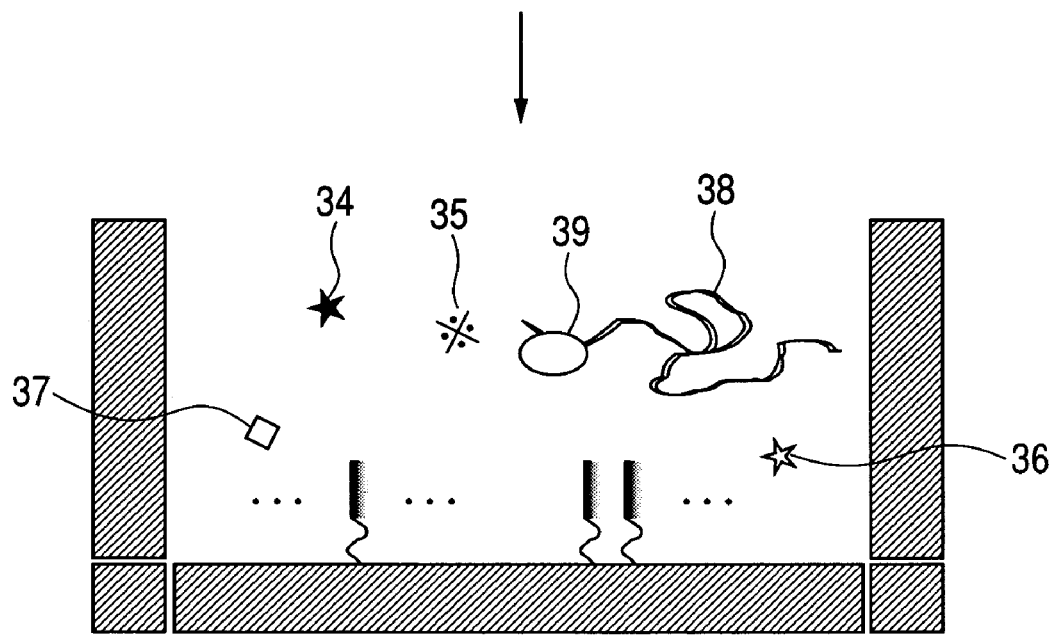
FIG. 9 shows a schematic diagram of PCR reaction using a reaction solution with a PCR reaction mixture containing dye terminator and a template double-strand DNA in PCR amplification reaction vessel with, on the bottom, microarrays of nucleic acid probes used in the detection method of SNPs and genetic polymorphisms according to the second embodiment of the present invention.

FIG. 9 schematically shows a reaction solution in the mode in which the DNA strands extended at the 3'-end of the nucleic acid probe are fluorescently labeled quantatively with the Dye terminators 34 to 37 when single-strand PCR amplification reaction is used in the method for detecting a single nucleotide polymorphism or genetic polymorphism according to the second embodiment of the present invention. As the reaction solution, DNA polymerase (Taq polymerase) 39, Dye terminators 34 to 37 corresponding to four nucleic acids and dNTPmix are added to the double-stranded DNA 38 of the sample extracted from the cell beforehand in a buffer solution for PCR reaction. Once the thermal cycle of PCR reaction starts, the double-stranded DNA 38 of the sample is dissociated into single-stranded DNAs in the denaturing step. Subsequently, the nucleic acid probe 33 bound to the carrier 31 for microarray via linker 32 connected to the 5'-end thereof hybridizes with a single-stranded DNA which has a complementary nucleotide sequence in the annealing step. On this occasion, as for the single-stranded DNA which has effected full-match hybridization with the nucleic acid probe 33, extension of a DNA strand begins from the 3'-end of the nucleic acid probe 33 by Taq polymerase using the single-stranded DNA as a template in the following extension step. When a nucleic acid of the corresponding Dye terminator is linked in place of dNTP in the extension step of the DNA strand, extension of the DNA strand thereafter is stopped. The resulting DNA strand extended at the 3'-end of the nucleic acid probe 33 is terminated with this Dye terminator, and as a result fluorescently labeled quantitatively. Once the thermal cycle of the following stage begins, the template single-stranded DNA is dissociate from the resulting DNA strand extended at the 3'-end of the nucleic acid probe 33 in the denaturing step. The same process was repeated henceforth and when the repetition of the thermal cycle was finished, as shown in FIG. 10, the corresponding parts of the nucleic acid probe 33 which exists on this spot becomes DNA strand extended at the 3'-end and one fluorescently labeled with the Dye terminator at the end.

Particularly, when a similar single-strand PCR amplification reaction is carried out by only adding Dye terminators 34 to 37 corresponding to four nucleic acids as the substrate of DNA polymerase (Taq polymerase) 39 without adding dNTPmix, the extension reaction stops in the state where one kind of Dye terminator corresponding to the next nucleotide is connected at the 3'-end of the nucleic acid probe 33. As a result, this spot is fluorescently labeled with this single kind of Dye terminator. Moreover, the extension of a DNA strand is immediately terminated by the connection of the Dye terminator, and the time required for extension step is significantly reduced as compared with a time period until a usual template single-stranded nucleic acid molecule reaches the 5'-end. Furthermore, since Tm value of a nucleic acid probe 33 with a small length of nucleotides is relatively low also in the denaturing step, dissociation to the template single-stranded nucleic acid molecule can be attained in a short time. As a result, the time required for denaturing step and extension step can be shortened, and a more high-speed thermal cycle can be selected.

Figure 10:
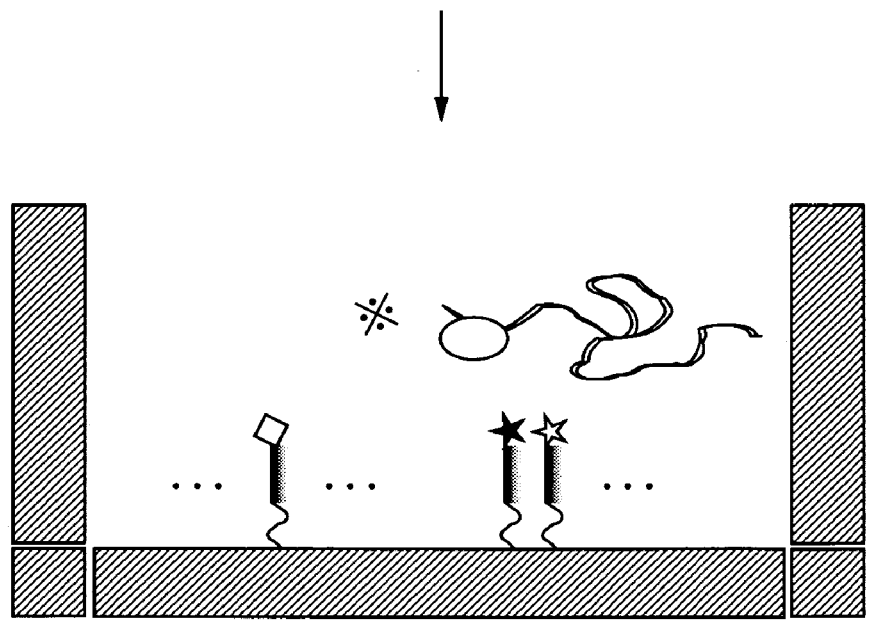
FIG. 10 shows a schematic diagram of fluorescent staining by dye terminator bound to the extending nucleic acid probes at the 3'-end, associated with PCR reaction using a reaction solution with a PCR reaction mixture containing dye terminator and a template double-strand DNA in the PCR amplification reaction vessel with, on the bottom, microarrays of nucleic acid probes used in the detection method of SNPs and genetic polymorphisms according to the second embodiment of the present invention.

FIGS. 8 to 10 illustrate a mode using a single-strand PCR amplification reaction with a nucleic acid probe bound through a linker connected to the 5'-end on the carrier surface as a primer. On the other hand, when multiplex PCR amplification reaction is used also with a primer to the complementary strand, a fluorescence label is introduced into a strand using usual fluorescently labeled dNTPmix and dUTP since double strand PCR amplification reaction is not performed using a Dye terminator. In this case, the fluorescence label introduced into the DNA strand extended at the 3'-end of the nucleic acid probe 33 is not quantitive, but it does not affect detection sensitivity. In addition, although the time period required for each stage of the thermal cycle becomes relatively longer in using a multiplex PCR amplification reaction since the extension of the complementary strand is necessary, the overall amplification efficiency itself becomes high at an accelerating pace. That is, in the case of using multiplex PCR amplification reaction, if the number of repetition of the thermal cycle is set to an decreased number and time required for the thermal cycle is made to a similar level as compared with the case where a single-strand PCR amplification reaction is used, it is possible to increase the production amount of the DNA strand extended at the 3'-end of the nucleic acid probe 33. Accordingly, although the multiplex PCR amplification reaction is used mainly in the case where the amount of the nucleic acid molecule to be detected existing in the primary sample is small, the amount of the DNA strand extended at the 3'-end of the nucleic acid probe 33 required for attaining sufficient detection sensitivity can be obtained by adjusting the time required for the thermal cycle to about dozens of minutes. Particularly, when aiming at use of multiplex PCR amplification reaction, it is possible to shorten the time required for the thermal cycle by using a reactor of the form illustrated in the above described which is excellent in the temperature response such as the PCR amplification reactor of the first embodiment of the present invention shown in FIG. 2.

In addition, the method for detecting a single nucleotide polymorphism or genetic polymorphism according to the second embodiment of the present invention has the following advantages as compared with the conventional microarray technology.

First, in the conventional microarray technology, PCR amplification reaction is performed as a pretreatment process by using the nucleic acid molecule of single nucleotide polymorphism or genetic polymorphism as a template, to amplify the DNA strand containing the nucleotide sequence portion beforehand by which each of the single nucleotide polymorphism or genetic polymorphism is characterized. In this pretreatment process, the DNA strand amplified is fluorescently labeled beforehand. For example, in the case where a fluorescence label is introduced into a strand using a usual dNTPmix and fluorescently labeled dUTP, the quantity of the fluorescence label introduced into the DNA strand amplified will generally show a large distribution. In addition, the fluorescence label introduced into the DNA strand amplified shows the same fluorescence wavelength.

Therefore, when misfit hybridization occurs to a nucleic acid probe in which a mismatch is shown in addition to the nucleic acid probe full-matched with a fluorescently labeled DNA strand to be detected in the hybridization with a nucleic acid probe, the difference in the fluorescence luminosity between the two might be indefinite depending on the variation in the quantity of the fluorescence label introduced into the DNA strand amplified.

On the contrary, according to the method for detecting a single nucleotide polymorphism or genetic polymorphism according to the second embodiment of the present invention, even a nucleotide sequence of a nucleic acid probe with which misfit hybridization occurs at high frequency will not be fluorescently labeled since extension of the DNA strand to 3'-end nucleotide does not proceed in the case where a nucleotide on the 3'-end of the nucleic acid probe immobilized on the carrier is mismatched with a single-stranded nucleic acid molecule of the sample. That is, the nucleotide sequence of the nucleic acid probe used for detection of single nucleotide polymorphism or genetic polymorphism has a broader degree of freedom in that one which does not show significant difference in the Tm value can be selected as long as the condition in which the nucleotide sequence of the nucleic acid probe is mismatched with at least a nucleotide on the 3'-end of a nucleotide sequence other than a mismatch to the 3'-end are the target mismatched nucleotide sequence.

Furthermore, temperature setup of hybridization reaction is performed in the conventional microarray technology in consideration of the difference of Tm value between the full-match and a mismatch, and performing a temperature setup of the optimal hybridization reaction to a large number of nucleic acid probes which constitute a microarray is not easy in many cases. On the contrary, according to the method for detecting a single nucleotide polymorphism or genetic polymorphism according to the second embodiment of the present invention, hybridization reaction is not used, and therefore, a large number of nucleic acid probes which constitute a microarray may have similar Tm values, which facilitates to find out the uniformity of reaction, and therefore allow a larger scope of application. From this advantage, the method for detecting a single nucleotide polymorphism or genetic polymorphism according to the second embodiment of the present invention will be a particularly effective method in the detection of single nucleotide polymorphism with few mismatched nucleotides.

In addition, in the mode using the single-strand PCR amplification reaction which effects fluorescence-labeling in the extension process of the above-mentioned DNA strand, even if a large amount of nucleic acid molecule which physically adsorb on the carrier surface exist in the primary sample, these nucleic acid molecules are not fluorescently labeled and will not cause interference as background fluorescence. Therefore, the processing for preventing the physical adsorption to the carrier surface also becomes unnecessary. Moreover, even if some variations are present in the fluorescence labeling efficiency in the extension step of the DNA strands, essential influence is not shown to the detection sensitivity.

Particularly, in the mode using a single-strand PCR amplification reaction, when the Dye terminators corresponding to four kinds of nucleotides are only used as substrate of DNA polymerase enzyme, and a technique is adopted in which one Dye terminator is directly linked to the 3'-end of a nucleic acid probe and thereby fluorescently labeled, it is possible to effect classification of the spots to be detected by colors (maximum of 4 colors) with the Dye terminators. Therefore, discerning power improves greatly from the case where the fluorescence label used is of one kind as in the conventional microarray technology. For example, in the polymorphism analysis of MHC in which heterogeneity exists etc., if two allelic genes originating in parents exist on the genome gene, it is necessary to detect both of them. According to the conventional microarray technology, usually used is one kind of fluorescence label, and therefore the results are superposed image of the two and accordingly it may become difficult to perform the distinction depending on the types of the target alleles. On the contrary, the distinction will be markedly easy by giving classification by color with the Dye terminators of maximum of 4 colors.

In addition, according to the method for detecting a single nucleotide polymorphism or genetic polymorphism according to the second embodiment of the present invention, not only a mode in which fluorescence labeling is effected in the process of extending a DNA strand at the 3'-end of a nucleic acid probe which is bound to the carrier surface through a linker connected to the 5'-end thereof, but also another mode can be selected in which once a DNA strand is extended at the 3'-end of a nucleic acid probe, detection is performed by using a fluorescently labeled secondary probe which hybridizes with this extended DNA strand highly quantitatively. As this secondary probe, for example, as for a group of nucleic acid molecules of single nucleotide polymorphism or genetic polymorphism, those having nucleotide sequence common with them can also be used. That is, according to the method for detecting a single nucleotide polymorphism or genetic polymorphism according to the second embodiment of the present invention, a fluorescently labeled secondary probe is used in order to show the existence of the DNA strand extended at the 3'-end of the nucleic acid probe bound to the carrier surface, and accordingly the specificity to the nucleotide sequence of each DNA strand is not needed. In another word, the flexibility with regard to the nucleotide sequence of the fluorescently labeled secondary probe is high, and setup of the hybridization condition will become very easy.

As explained above, the method for detecting a single nucleotide polymorphism or genetic polymorphism according to the second embodiment of the present invention can significantly shorten the time for of PCR amplification reaction which is performed in the detection process while maintaining the large-scale array suitable for use of a large number of nucleic acid probes which are the features of the microarray technology. In addition, in case the single-strand PCR amplifying method is applied, the detection sensitivity is improved and it can be applied also as non-interfering multiplex PCR amplification. In the meantime, the fall of the detection sensitivity resulting from background fluorescence is also avoided and therefore it is a method useful particularly when the SNPs and/or polymorphisms are analyzed.

EXAMPLES

The present invention will be described more specifically below with examples. Examples described below represent one of the best examples according to the present invention, but the present invention is not limited to these examples.

Example 1-1

In the present Example 1-1, prepared was a PCR reaction vessel having a micro heater wire capable of directly heating a PCR reaction solution built in a commercially available PCR vessel.

First, nichrome wire heater ($\Phi=230$ μm, 26 Ω/m) was coiled around a piano wire ($\Phi=500$ μm), and a coiled nichrome wire heater (coil interval: about 500 μm, outside diameter of coil: about 1000 μm, length of coil part: 10 mm) was formed. This coil heater 1 was installed in a commercially available PCR vessel with a volume of 200 μl. For fixing the coil heater 1 to the PCR vessel, the heater was energized and locally heated, and the vicinity of a mouth of a resin vessel was melted to fix the end of the heater wire. This PCR vessel 3 having the micro heater wire built in is used while being inserted in a hole of a heating block 5 for fixation. This heating block 5 itself has a large heat capacity, and is heated and kept at a constant temperature. Therefore, while the coil heater 1 is not energized, the entire micro heater wire built-in PCR vessel 3 is kept at a desired annealing temperature. On the other hand, when the coil heater 1 is energized and locally heated and then the energization is stopped, rapid heat release occurs through thermal conductivity from the PCR vessel 3 to the heating block 5.

To the micro heater wire built-in PCR vessel 3, 25 μl of pure water was added. Then, a square wave pulse voltage with a pulse width of 100 ms and a period of 1 Hz was applied to the heater wire and the pulse voltage was gradually increased. At that time, when a pulse height value reached to 43 V, it was confirmed that foaming caused by water vaporization was observed. Thus, under the above pulse voltage application conditions, it was confirmed that pure water in the PCR vessel and near the coil heater was heated to a boiling point (100° C.) at the end of applied pulse time. In other words, at the beginning of the applied pulse, the temperature of the pure water was initially as low as room temperature. However, during the applied pulse time, the pure water was gradually heated to increase its temperature. At the final point of the applied pulse time, the temperature of the pure water increased to a boiling point (100° C.). Thereafter, during the period of 900 ms of no voltage application, the heat was gradually released and the pure water temperature was decreased to a level of not higher than 50° C. just before a subsequent applied pulse.

The above conditions were programmed in a pulse voltage application apparatus 4, and as a PCR cycle, a pulse voltage to be applied to the coil heater was set with a repetition period of 1 Hz, a pulse height value of 43 V, a pulse width of 100 ms, and the repetition number of 30 times. A reaction solution having the following composition was added to the manufactured micro heater built-in PCR vessel 3.

TABLE 1

Composition of Reaction Solution

| Component | | Amount |
|---|---|---|
| PCR reaction mixture | PCRmix (Qiagen Inc.) | 12.5 µl |
| Template | pUC118/EcoRI (Takara Shuzo Co., Ltd.) | 1 µl |
| Forward primer | 5'-GAGTCGACCTGCAGGCAT-3' | 1 µl |
| Reverse primer | 5'-TAAGTTGGGTAACGCCAG-3' | 1 µl |
| Pure water | | 9.5 µl |
| Total | | 25.0 µl |

Figure 4:
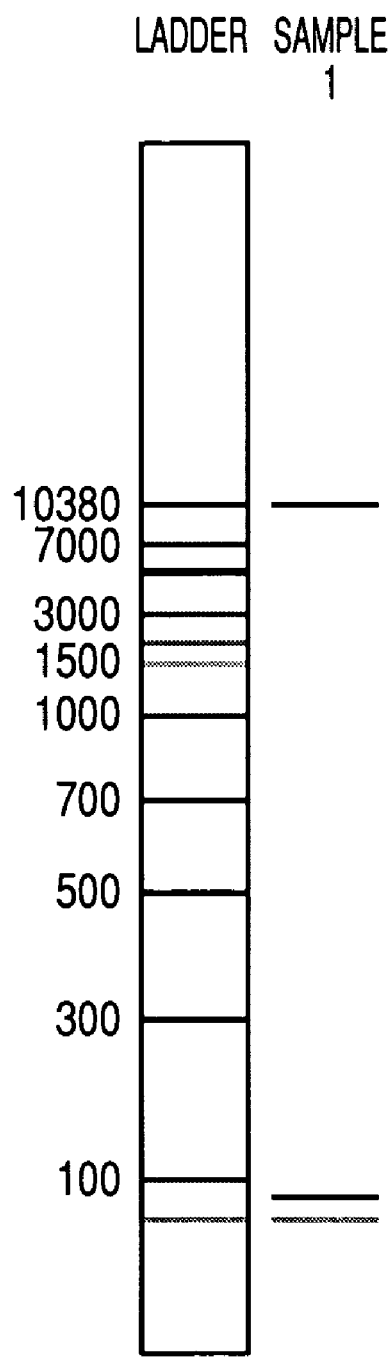
FIG. 4 shows the result of analysis by the electrophoresis of the PCR amplification reaction product obtained by the PCR reaction shown in Example 1-1.

This reaction solution 2 was subjected to the PCR cycle described above to amplify DNA fragments. FIG. 4 shows a result of analysis on a sample containing the PCR product by electrophoresis (Bioanalyzer, Agilent Technologies). When reference was made on the nucleotide sequence of a template of plasmid pUC118 and the nucleotide sequence of the PCR primer pairs, a band was confirmed near approximately 85 bp, corresponding to the size of a target PCR amplification product.

Example 1-2

In this Example 1-2, a laminated structure of $SiO_2/polySi/SiO_2$ was formed on a silicon wafer. The polysilicon film was used as a heater layer. Further, on the surface thereof, a heat release silicone rubber sheet with a hollow internally provided was laminated, thereby producing a plate-like PCR reaction vessel.

First, a silicon wafer was cut into pieces each having a standard size of ordinary microscopic slide glass (height×width=25 mm×75 mm). On the surface thereof, a $SiO_2$ film (lower insulation layer) with a film thickness of 0.1 µm was formed using an RF sputtering apparatus in the conditions of: atmosphere: 80% Ar-20% $O_2$, pressure: 5 mTorr, and applied RF power: 6 W/cm$^2$.

On the surface of the $SiO_2$ film (lower insulation layer), a 1-µm polysilicon film was formed by RF sputtering method in the film formation conditions of Table 2 while Si was regarded as a target.

TABLE 2

RF sputtering film formation conditions

| Film formation condition | Setting value |
|---|---|
| Kind of sputtering gas (flow rate) | Ar 200 normal-mL/s |
| | $H_2$ 20 normal-mL/s |
| Substrate temperature | 150° C. |
| Target Bias | −180 V |
| Substrate bias | 10 V |

TABLE 2-continued

RF sputtering film formation conditions

| Film formation condition | Setting value |
|---|---|
| Electricity supplied (Rf frequency) | 100 W/100 MHz |
| Film formation rate | 25 nm/min |

Further, on the surface of the polysilicon film, a $SiO_2$ film with a thickness of 0.1 µm was formed as an upper insulation layer in the same condition as for the lower insulation layer of $SiO_2$ film, resulting in the laminated structure of $SiO_2/polySi/SiO_2$.

In the meantime, a heat release silicone rubber sheet with a thickness of 1.0 mm was processed to have an outer shape with a smaller size by 5 mm in width than the slide glass standard (height×width=25 mm×70 mm) and a rectangular hollowed part of height×width=20 mm×30 mm inside itself. The heat release silicone rubber sheet was closely attached on the silicon wafer having a laminated structure of $SiO_2/polySi/SiO_2$ on its surface. Therefore, the hollowed part of the heat release silicone rubber sheet became a pool-like vessel part with a depth of 1.0 mm for storing a sample solution. On top of that, a silicon wafer with height×width=20 mm×70 mm was placed as a lid part so as to hermetically seal the vessel. In this vessel, the polysilicon film among the laminated structure of $SiO_2/polySi/SiO_2$ is used as a heater layer, and the pool-like vessel is heated from the bottom.

The heater-attached PCR vessel 3 was used while it was closely attached onto the heating block 5. This heating block 5 itself has a large heat capacity, and is heated and kept at a constant temperature. Therefore, while a sheet-like heater 1 is not energized, the entire of the heater-attached PCR vessel 3 is kept at a desired annealing temperature. On the other hand, when the sheet-like heater 1 is energized for local heating and then the energization is stopped, rapid heat release occurs through thermal conductivity from the PCR vessel 3 to the heating block 5.

Figure 7:
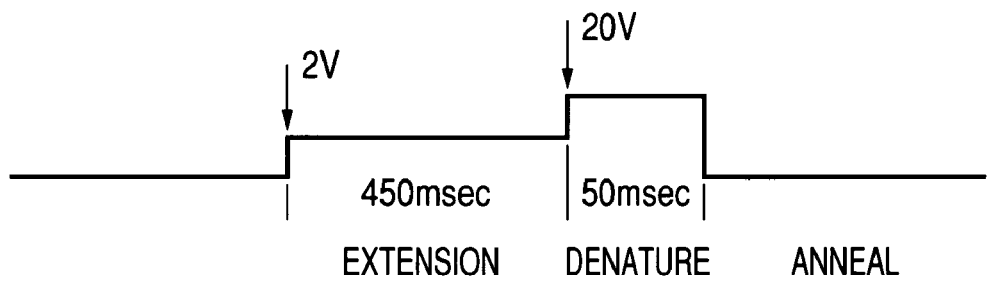
FIG. 7 shows the form of pulsed voltage applied to the heater for local heating in a thermal cycle used in the PCR reaction shown in Example 1-2.

In a PCR cycle, a pulse voltage, shown in FIG. 7, to be applied to the polysilicon film heater was set with the repetition number of 30, and the cycle had a repetition period of 1 Hz for extension at an applied voltage of 2 V for 450 ms, denaturation at 20 V for 50 ms, and annealing at 0 V for 500 ms. Into the manufactured heater-attached PCR vessel, a reaction solution having the following composition was added.

TABLE 3

Composition of reaction solution

| Components | | Amount |
|---|---|---|
| PCR reaction mixture | PCRmix (Qiagen Inc.) | 25 µl |
| Template | pUC118/EcoRI (Takara Shuzo, Co., Ltd.) | 2 µl |
| Forward primer | 5'-GCGGTAATACGGTTATCCAC-3' | 2 µl |
| Reverse primer | 5'-TAAGTTGGGTAACGCCAG-3' | 2 µl |
| Pure water | | 19 µl |
| Total | | 50 µl |

Figure 5:
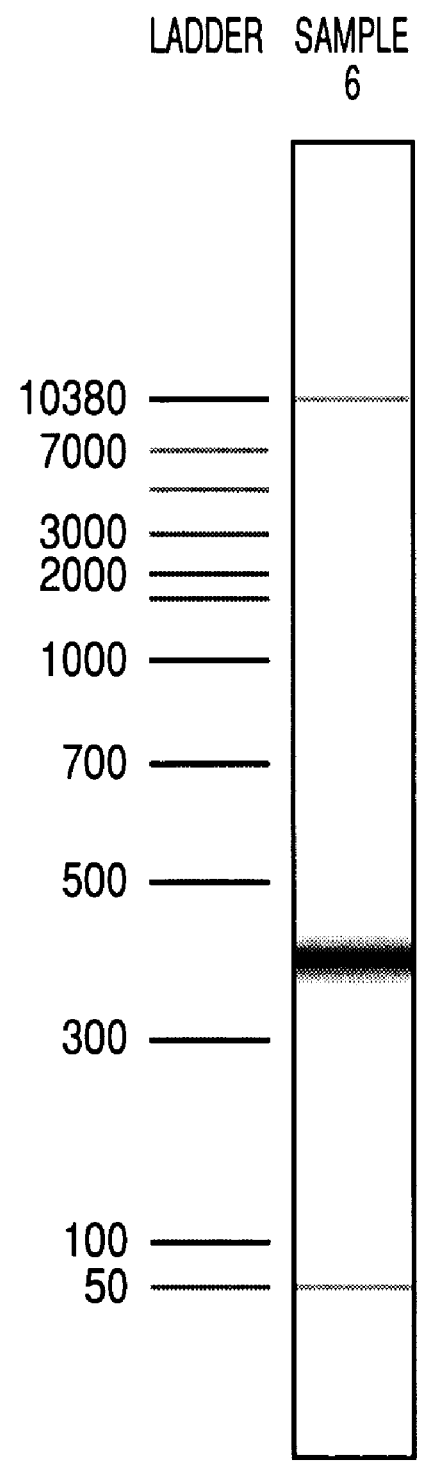
FIG. 5 shows the result of analysis by the electrophoresis of the PCR amplification reaction product obtained by the PCR reaction shown in Example 1-2.

50 µl (50 mm$^3$) of this reaction solution was poured into the hollowed part with 20 mm×30 mm, and the above-mentioned PCR cycle was carried out to amplify DNA fragments. FIG. 5 shows a result of analysis on a sample containing the PCR product by electrophoresis (Bioanalyzer, Agilent Technologies). When reference was made on the nucleotide sequence of a template of plasmid pUC118 and the nucleotide sequence of the PCR primer pairs, a band was confirmed near approximately 350 bp, corresponding to the size of a target PCR amplification product.

Example 2-1

[Manufacturing of PCR Reaction Vessel]

In this Example 2-1, a heat release silicone rubber sheet with a hollow internally provided was laminated on the surface of a silicon wafer, thereby manufacturing a plate-like PCR reaction vessel.

First, a silicon wafer was cut into a piece having a standard size of ordinary microscopic slide glass (height×width=25 mm×75 mm). Further, a heat release silicone rubber sheet with a thickness of 1.0 mm was processed so that it has an outer shape with the same size as the slide glass standard (height×width=25 mm×70 mm) and it also has a rectangular hollowed part of height×width=20 mm×30 mm inside itself. The heat release silicone rubber sheet was closely attached onto the silicon wafer having the above rectangular shape. Thus, the hollowed part of the heat silicone rubber sheet became a pool-like vessel part with a depth of 1.0 mm for storing a sample solution. On top of that, a silicon wafer having the same slide glass standard size as above was placed as a lid part so as to hermetically close the pool-like vessel part.

[Preparation of Microarray]

(Introduction of Functional Group into the Silicon Wafer Surface)

Functional groups used for DNA probe fixation were introduced into the surface of the rectangular silicon wafer having a slide glass standard size according to the following procedures.

First, the rectangular silicon wafer was subjected to ultrapure water/ultrasonic cleaning for 5 minutes. An aminosilane coupling agent aqueous solution was prepared by adding a silane coupling agent KBM-603 (manufactured by Shin-Etsu Silicones) to pure water to a concentration of 1%, starring at room temperature for 2 hours for dissolution. Subsequently, the cleaned rectangular silicon wafer was immersed in the silane coupling agent solution, and left standing at room temperature for 20 minutes. After this immersion treatment, the silicon wafer was taken out from the solution and the surface thereof was lightly washed with pure water. Then, nitrogen gas was blown to both surface of the rectangular silicon wafer for drying. Next, the dried rectangular silicon wafer was baked for 1 hour in an oven heated at 120° C. This baking treatment completes reaction of the coupling agent with the surface of silicon wafer, and thus an amino group derived from the silane coupling agent was introduced to the surface of the silicon wafer.

Next, N-(6-maleimidocaproyloxy)succinimide (hereinafter abbreviated as EMCS) (manufactured by Dojindo Laboratories) was dissolved in a mixed solvent of dimethyl sulfoxide and ethanol (1:1) to a final concentration of 0.3 mg/ml, and thereby an EMCS solution was prepared. After the baking treatment was completed, the silicon wafer was allowed to stand while cooling and immersed in the prepared EMCS solution at room temperature for 2 hours. During this immersion treatment in EMCS solution, the silane coupling agent-derived amino group introduced onto the surface thereof was reacted with the succinimide group of EMCS to introduce a maleimide group to the surface of the silicon wafer. The rectangular silicon wafer taken out from the EMCS solution was washed with the mixed solvent of dimethyl sulfoxide and ethanol (1:1) to remove unreacted EMCS, and further washed with ethanol to remove the mixed solvent. Thereafter, the silicon wafer having a maleimide group introduced into its surface was dried.

(Preparation of Probe DNA)

Gene data relating to BRB1 of HLA was obtained from a web site (http://www.ebi.ac.uk/imgt/hla/) of Data Bank EBI (The European Bioinformatics Institute), wherein published gene information is registered to select four probe nucleotide sequences for identifying the following alleles.

```
>DRB1*0804
5'-cggtgacggagctggggcggcctg

>DRB1*0407
5'-tgcagacacaactacggggttggt

>DRB1*1303
5'-gtgacggagctggggcggcctagc

>DRB1*0301
5'-atacttccataaccaggaggagaa
```

Synthesis of a probe DNA having a selected nucleotide sequence was conducted at a DNA synthesis manufacturer. In addition, an SH group was introduced in advance into the 5'-end of a probe DNA to be synthesized. For this SH group introduction, a commercially available thiol modifier (Glen Research Corporation) was used. This allowed a sulfanyl group (—SH) to be introduced as a linker chain into the 5'-end of an oligonucleotide chain: NNNNNNNNNN, which was solid phase synthesized, via —$(CH_2)_6$— in the form of 5'-HS—$(CH_2)_6$—O—$PO_2$—O—NNNNNNNNNN-3'.

Meanwhile, the 3'-end of each probe contains mismatch from nucleotide sequence of other alleles, and additionally, selection of its nucleotide sequence was conducted after consideration was given so that a base indicating each mismatch was 4 kinds, A, C, T, and G. The synthesized probe DNAs were dissolved in an aqueous solution of 5% glycerin and 1% Acetylenol EH (Kawaken Fine Chemicals Co., Ltd.) so that the DNA concentration corresponded to an absorbance of 0.4 OD (absorbance wavelength 260 nm). The prepared probe DNA solution was filled in an ink tank for Bubble Jet Printer (trade name: BJF-850, Canon Inc.). This Bubble Jet Printer can spot droplets containing some picoliters of probe DNA at minimum dot pitch of about 120 μm by inputting a printing pattern according to a specified file creation process.

(Preparation of Microarray)

The droplets containing probe DNA were spotted on the above-described silicon wafer having functional groups introduced therein so that the silicon wafer became a microarray having the total of 16 dots (4 dots for 1 probe DNA). After spotting, it was left standing in a humidified chamber for 30 minutes to react a maleimide group on the surface of the silicon wafer with a sulfanyl group (—SH) of 5'-end of probe DNA. Thereafter, unreacted probe DNAs remaining on the surface of the silicon wafer were washed with 10 mM phosphate buffer solution (pH 7.0) containing 100 mM of NaCl. A microarray was obtained wherein each oligonucleotide chain was immobilized at 5'-end via a linker chain —$(CH_2)_6$— on the silicon wafer surface.

[Preparation of Sample Solution]

From IHWG (International Histocompatibility Working Group), 4 kinds of panel cells in the following table were obtained. Each panel cell was suspended in a cell suspension (10 mM Tris-HCl pH 7.6, 10 mM EDTA, and 50 mM NaCl)

so as to have a cell density of 10×10⁶/ml. Then, 0.5 ml of this cell suspension was taken as a sample. To the sample, 50 µl of proteinase K solution (10 mg/ml dissolved in dH$_2$O) and 50 µl of 10% SDS (dissolved in dH$_2$O) were added, and the mixture was incubated at 45° C. for 3 hours.

Further, 0.6 ml of PCI (phenol chloroform isoamyl alcohol=25:24:1) was added in equal proportions, and the mixture was shaken for 10 minutes to terminate cell breakage. After the cell breakage, operation of collecting an aqueous layer into other tube was repeated twice. The collected soluble fraction (aqueous layer) sample was subjected to ordinary ethanol precipitation so that nucleic acid chain contained therein was deposited. Thereafter, precipitates of the deposited nucleic acid chain were vacuum-centrifuged for simple drying.

TABLE 4

| Panel cell (13th WS No.) | HLA-DRB1 |
| --- | --- |
| 9381 | 0301; 0407 |
| 9030 | 0407 |
| 9297 | 1303 |
| 9398 | 1303; 0804 |

[Detection Reaction of Target Substance by PCR]

The precipitates of the nucleic acid chains separated by the above sample preparation contain genome genes of each panel cell. To the precipitate samples of nucleic acid chains, which were dehydrated and dried in a tube vessel, 40 µl of PCR reaction mixture (BigDye Terminator v3.0 Cycle Sequencing Ready Reaction Kit, ABI) and 160 µl of buffer (Sequencing Buffer, ABI) were added and mixed, thereby obtaining a reaction solution. 200 µl of the reaction solution was poured into the PCR reaction vessel made of the above-described rectangular silicon wafer having a microarray formed on its surface, and the chamber was closely sealed with a rectangular silicon wafer lid for preventing evaporation. The reaction solution in this reaction chamber was subjected to single-strand DNA amplification reaction by temperature cycle of the following Table 5.

TABLE 5

| | Temperature cycle | | |
| --- | --- | --- | --- |
| Operation step | Temperature | Time | Repetition number |
| denature | 96° C. | 5 s | |
| denature | 96° C. | 1 s | |
| anneal | 50° C. | 1 s | 100 times |
| extension | 60° C. | 1 s | |
| pool | 4° C. | Retain | |

After the above single-strand DNA amplification reaction was terminated, the surface of rectangular silicon wafer having the microarray formed in the reaction chamber was washed on a shaker with 70% ethanol for 1 minute. This washing was conducted twice. The washing solution was removed by centrifugation, and the microarray region formed on the surface of the rectangular silicon wafer was observed by fluorescence microscope. In other words, in the DNA sample which was prepared from the panel cell and contains genome genes, a DNA chain was extended at the 3'-end of a probe DNA corresponding to an allele of HLA-DRB1, and dye terminator was bound to that end. Along with such DNA chain extension, Table 6 summarizes results of observation on the presence or absence of fluorescence attributable to dye terminator, which is bound to the 3'-end side of a probe DNA.

TABLE 6

| Specimen (panel cell) | DRB1*0804 | DRB1*0407 | DRB1*1303 | DRB1*0301 |
| --- | --- | --- | --- | --- |
| 9381 | − | + | − | + |
| 9030 | − | + | − | − |
| 9297 | − | − | + | − |
| 9398 | + | − | + | − |

In view of the above results, it has been confirmed that only spots of probe DNAs that correspond to alleles contained in each panel cell and can hybridize with genes of those alleles were successful in single-strand DNA amplification reaction and were stained with fluorescence.

The PCR reaction method of the present invention can be used to enhance efficiency of PCR amplification reaction of nucleic acid chains used in the field such as life science and biotechnology.

In addition, the method for detecting a nucleic acid using PCR amplification reaction of the present invention can be a nucleic acid detection method using a DNA microarray, which can be applied to the detection of mutations or mismatched nucleotides such as genomic diversity, genetic polymorphism and single nucleotide polymorphism.

The present invention is not limited to the above examples and various changes and modifications can be made within the spirit and scope of the present invention. Therefore to apprise the public of the scope of the present invention, the following claims are made.

This application claims priority from Japanese Patent Application No. 2004-130041 filed on Apr. 26, 2004, which is hereby incorporated by reference herein.

What is claimed is:

1. A method for PCR amplification reaction comprising the steps of:
 preparing a reaction vessel in which a heater is placed at a position to come into direct contact with a reaction solution containing a nucleic acid chain;
 preparing a heating block in which the reaction vessel is held;
 maintaining the heating block at a temperature corresponding to an annealing phase;
 setting the reaction solution into the reaction vessel; and
 applying a row of pulsed current to the heater during a denaturing phase for producing pulsed heating corresponding to a pulse time width and a pulse current height of the row of pulsed current to directly heat the reaction solution with the pulsed heating,
 wherein the heater is a coiled heater and is placed in the reaction vessel.

2. The method for PCR amplification reaction according to claim 1, wherein the reaction solution is stored in a solution storing section of the reaction vessel, at a designed storing capacity of the solution storing section, and wherein the storing capacity of the solution storing section and a shape of the solution storing section are designed in order to exhibit a heat capacity in which the temperature of the reaction solution can respond to a thermal pulse generated by applying a predetermined row of pulsed current to the heater in the order of at least 0.01 second.

3. The method for PCR amplification reaction according to claim 1, wherein application of the row of pulsed current is repeated a plurality of times periodically and the pulsed heating is correspondingly repeated a plurality of times.

4. A method for PCR amplification reaction comprising the steps of:
 preparing a reaction vessel in which a heater is placed at a position to come into direct contact with a reaction solution containing a nucleic acid chain;
 setting the reaction solution into the reaction vessel;
 preparing a heating block in which the reaction vessel is held;
 maintaining the heating block at a temperature corresponding to an annealing phase; and
 applying a row of pulsed current to the heater during a denaturing phase for producing pulsed heating corresponding to a pulse time width and a pulse current height of the row of pulsed current to directly heat the reaction solution with the pulsed heating,
 wherein the heater is a film and is placed in an inner surface of the reaction vessel.

5. The method for PCR amplification reaction according to claim 4, wherein the reaction solution is stored in a solution storing section of the reaction vessel, at a designed storing capacity of the solution storing section, and wherein the storing capacity of the solution storing section and a shape of the solution storing section are designed in order to exhibit a heat capacity in which the temperature of the reaction solution can respond to a thermal pulse generated by applying a predetermined row of pulsed current to the heater in the order of at least 0.01 second.

6. The method for PCR amplification reaction according to claim 4, wherein application of the row of pulsed current is repeated a plurality of times periodically and the pulsed heating is correspondingly repeated a plurality of times.

* * * * *

SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: Synthesized DNA probe

<400> SEQUENCE: 1

-continued

```
gtgacggagc tggggcggcc tagc                                              24

<210> SEQ ID NO 2
<211> LENGTH: 24
<212> TYPE: DNA
<213> ORGANISM: Artificial Sequence
<220> FEATURE:
<223> OTHER INFORMATION: Synthesized DNA probe

<400> SEQUENCE: 2
tgcagacaca actacggggt tggt                                              24

<210> SEQ ID NO 3
<211> LENGTH: 24
<212> TYPE: DNA
<213> ORGANISM: Artificial Sequence
<220> FEATURE:
<223> OTHER INFORMATION: Synthesized DNA probe

<400> SEQUENCE: 3
gtgacggagc tggggcggcc tagc                                              24

<210> SEQ ID NO 4
<211> LENGTH: 24
<212> TYPE: DNA
<213> ORGANISM: Artificial Sequence
<220> FEATURE:
<223> OTHER INFORMATION: Synthesized DNA probe

<400> SEQUENCE: 4
atacttccat aaccaggagg agaa                                              24
```